United States Patent [19]
Aurelian

[11] Patent Number: 6,013,265
[45] Date of Patent: Jan. 11, 2000

[54] VACCINE COMPOSITION FOR HERPES SIMPLEX VIRUS AND METHODS OF USING

[75] Inventor: Laure Aurelian, Baltimore, Md.

[73] Assignee: University of Maryland, Baltimore, Baltimore, Md.

[21] Appl. No.: 08/956,254

[22] Filed: Oct. 22, 1997

Related U.S. Application Data

[60] Provisional application No. 60/029,093, Oct. 22, 1996.

[51] Int. Cl.$^7$ .......................... A61K 39/245; A61K 39/12
[52] U.S. Cl. ..................................... 424/231.1; 424/229.1; 424/204.1; 424/199.1; 424/205.1; 435/320.1; 435/235.1; 536/23.72
[58] Field of Search .............................. 424/199.1, 204.1, 424/205.1, 229.1, 231.1; 435/320.1, 235.1; 536/23.72

[56] References Cited

PUBLICATIONS

Parr et al. Labrotory Investigation. 1994, vol. 70, No. 3, pp. 369–380.
Milligan et al. Virology, 1995, vol. 206, pp. 234–241.
Murthy et al. Journal of Virology, 1989, vol. 63, No. 8, pp. 3307–3314.

*Primary Examiner*—Mary E. Mosher
*Assistant Examiner*—Ali R. Salimi
*Attorney, Agent, or Firm*—William S. Ramsey

[57] ABSTRACT

The present invention discloses a new vaccine composition for HSV-1 and HSV-2 comprising a whole live HSV-2 virus having the oncogene deleted. Methods of using the vaccine composition are also included.

9 Claims, 12 Drawing Sheets

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      HYBRIDIZATION PROBE CORRESPONDING TO ICP10RR CODING REGION OF
      HSV-2

<400> SEQUENCE: 1
ccccttcatc atgtttaagg a                                              21

<210> SEQ ID NO 2
<211> LENGTH: 446
<212> TYPE: PRT
<213> ORGANISM: herpes simplex virus-2
<220> FEATURE:
<221> NAME/KEY: DOMAIN
<222> LOCATION: (1)..(446)
<223> OTHER INFORMATION: PROTEIN KINASE DOMAIN OF ICP10 SUBUNIT OF
      HSV-2
<300> PUBLICATION INFORMATION:
<301> AUTHORS: CHUNG ET AL.,
<303> JOURNAL: J. Virol.
<304> VOLUME: 63
<306> PAGES: 3389-3398
<307> DATE: 1989
<300> PUBLICATION INFORMATION:
<301> AUTHORS: NELSON ET AL.,
<303> JOURNAL: J. Biol. Chem.
<304> VOLUME: 271
<306> PAGES: 17021-17027
<307> DATE: 1996
```

```
<400> SEQUENCE: 2

Met Ala Asn Arg Pro Ala Ala Ser Ala Leu Ala Gly Ala Arg Ser Pro
 1               5                  10                  15

Ser Glu Arg Gln Glu Pro Arg Glu Pro Glu Val Ala Pro Pro Gly Gly
                20                  25                  30

Asp His Val Phe Cys Arg Lys Val Ser Gly Val Met Val Leu Ser Ser
            35                  40                  45

Asp Pro Pro Gly Pro Ala Ala Tyr Arg Ile Ser Asp Ser Ser Phe Val
        50                  55                  60

Gln Cys Gly Ser Asn Cys Ser Met Ile Ile Asp Gly Asp Val Ala Arg
 65                  70                  75                  80

Gly His Leu Arg Asp Leu Glu Gly Ala Thr Ser Thr Gly Ala Phe Val
                85                  90                  95

Ala Ile Ser Asn Val Ala Ala Gly Gly Asp Gly Arg Thr Ala Val Val
            100                 105                 110

Ala Leu Gly Gly Thr Ser Gly Pro Ser Ala Thr Thr Ser Val Gly Thr
        115                 120                 125

Gln Thr Ser Gly Glu Phe Leu His Gly Asn Pro Arg Thr Pro Glu Pro
130                 135                 140

Gln Gly Pro Gln Ala Val Pro Pro Pro Pro Pro Pro Phe Pro Trp
145                 150                 155                 160

Gly His Glu Cys Cys Ala Arg Arg Asp Ala Arg Gly Gly Ala Glu Lys
                165                 170                 175

Asp Val Gly Ala Ala Glu Ser Trp Ser Asp Gly Pro Ser Ser Asp Ser
            180                 185                 190

Glu Thr Glu Asp Ser Asp Ser Ser Asp Glu Asp Thr Gly Ser Gly Ser
        195                 200                 205

Glu Thr Leu Ser Arg Ser Ser Ser Ile Trp Ala Ala Gly Ala Thr Asp
    210                 215                 220

Asp Asp Asp Ser Asp Ser Asp Ser Arg Ser Asp Ser Val Gln Pro
225                 230                 235                 240

Asp Val Val Arg Arg Arg Trp Ser Asp Gly Pro Ala Pro Val Ala
                245                 250                 255

Phe Pro Lys Pro Arg Arg Pro Gly Asp Ser Pro Gly Asn Pro Gly Leu
                260                 265                 270

Gly Ala Gly Thr Gly Pro Gly Ser Ala Thr Asp Pro Arg Ala Ser Ala
            275                 280                 285

Asp Ser Asp Ser Ala Ala His Ala Ala Pro Gln Ala Asp Val Ala
290                 295                 300

Pro Val Leu Asp Ser Gln Pro Thr Val Gly Thr Asp Pro Gly Tyr Pro
305                 310                 315                 320

Val Pro Leu Glu Leu Thr Pro Glu Asn Ala Glu Ala Val Ala Arg Phe
                325                 330                 335

Leu Gly Asp Ala Val Asp Arg Glu Pro Ala Leu Met Leu Glu Tyr Phe
            340                 345                 350

Cys Arg Cys Ala Arg Glu Glu Ser Lys Arg Val Pro Pro Arg Thr Phe
        355                 360                 365

Gly Ser Ala Pro Arg Leu Thr Glu Asp Phe Gly Leu Leu Asn Tyr
370                 375                 380

Ala Leu Ala Glu Met Arg Arg Leu Cys Leu Asp Leu Pro Pro Val Pro
385                 390                 395                 400

Pro Asn Ala Tyr Thr Pro Tyr His Leu Arg Glu Tyr Ala Thr Arg Leu
                405                 410                 415
```

-continued

```
Val Asn Gly Phe Lys Pro Leu Val Arg Arg Ser Ala Arg Leu Tyr Arg
            420                 425                 430

Ile Leu Gly Ile Leu Val His Leu Arg Ile Arg Thr Arg Glu
            435                 440                 445
```

VACCINE COMPOSITION FOR HERPES SIMPLEX VIRUS AND METHODS OF USING

This application claims priority to U.S. Provisional Patent Application Ser. No. 60/029,093, filed Oct. 22, 1996.

BACKGROUND OF THE INVENTION

Herpes Simplex Virus (HSV) is a well-studied virus. Both distinguishable serotypes of Herpes Simplex Virus (HSV-1 and HSV-2) cause infection and disease ranging from relatively minor fever blisters on lips to severe genital infections, and generalized infections on newborns. HSV-1 and HSV-2 are 50% homologous at the DNA level, and polyclonal antibodies and MAbs to shared epitopes for one are cross-reactive to the other.

HSV-1 and HSV-2 have RR1 proteins (respectively designated ICP6 and ICP10) that contain a unique amino terminal domain. The HSV-2 unique domain codes for a ser/thr-specific PK which has auto- and transphosphorylating activity and has a transmembrane domain. Sequences which code for the PK domain cause neoplastic transformation and are associated with cervical cancer (HSV-2 oncogene). The unique terminal domain of the HSV-1 RR1 protein (ICP6) also has PK activity but it is different from that of the HSV-2 oncogene both structurally and functionally.

Original studies, using enzymatic assay conditions similar to those employed for ICP10 PK, concluded that ICP6 does not have PK activity, although the unique domain is retained (Chung et al., J. Virol. 63:3389–3398, 1989). This was not unexpected since the sequence of the unique PK domains showed only 38% homology (Nikas et al., Proteins:Structure, function and genetics 1:376–384, 1986). Further studies indicated that ICP6 has PK activity but only under different conditions. Also there is controversy as to whether the activity is both auto- and transphosphorylating (see Peng et al., Virology 216:184–196, 1996 for a review of the problem; particularly Table 1). The reason for the different PK activities of the ICP6 and ICP10 proteins is likely to be that the ICP6 PK has its ATP binding sites located distantly from the rest of the catalytic motifs (Cooper et al., J. Virol. 69:4979–4985, 1995). ICP6 also does not have a TM domain and it does not localize to the cell surface (Conner et al., Virology 213:615, 1995). The PK activity of native ICP6 is very weak even under ideal conditions, such that its $K_m$ is 10-fold higher than that of ICP10 PK (Peng et al., Virology 216:184, 1996; Lee and Aurelian, in preparation).

The transforming activity of ICP6 is located within a genome fragment that is distant from that at which the HSV2 oncogene is located. Transformation in this system is only based on focus formation.

It has previously been shown that HSV-2 protein kinase activity is localized at amino acids 1–446 (Chung et al., J. Virol. 63:3389–3398, 1989). Cells which express a protein consisting of ICP10 amino acids 1–446 evidence anchorage independent growth and neoplastic growth. Therefore, the HSV-2 oncogene is located at the DNA sequence encoding ICP10 (SEQ ID NO:2) amino acids 1–446 (Smith et al., Virology 200:598–612, 1994).

Protein kinase (PK) activity is required for neoplastic transformation (Smith et al., Virology 200:598–612, 1994). Transformation is seen in both rodent and human cells (Jariwalla et al., PNAS 77:2279–2283, 1980; Hayashi et al., PNAS 82:8493–8497, 1985; Smith et al., Virology 200:598–612, 1994). Studies therefore have demonstrated that the HSV-2 oncoprotein is located at ICP10 amino acids 1–446.

The minimal ICP10 size required for PK activity is at amino acids 1–283 (pp29$^{la1}$) (Luo et al., *J. Biol. Chem.* 266: 20976–20983, 1991). The PK activity of pp29$^{la1}$ has some properties different from the authentic ICP10 PK (Luo et al., *J. Biol. Chem.* 266: 20976–20983, 1991). The minimal size of the ICP10 transforming protein (HSV-2 oncogene) is at amino acids 1–446. It has been shown that the PK domain encompasses eight catalytic motifs and SH3-binding sites which are involved in interaction with signaling proteins and is located at ICP10 amino acids 1–446 (Chung et al., J. Virol. 63:3389–3398, 1989; Nelson et al., J. Biol. Chem. 271:17021–17027, 1996).

It has also previously been shown that the HSV-2 oncoprotein has intrinsic PK activity. This was shown by demonstrating that ICP10 PK activity is lost through site-directed mutagenesis. The oncogene also has SH3-binding domains at positions 140, 149 and 396, which are required for interaction with signaling proteins. This interaction is required for transforming activity. Site directed mutagenesis was used to identify amino acids required for kinase activity and interaction with signaling proteins. Mutation of Lys$^{176}$ or Lys$^{259}$ reduced PK activity (5–8 fold) and binding of the $^{14}$C-labeled ATP analog p-fluorosulfonylbenzoyl 5'-adenosine (FSBA), but did not abrogate them. Enzymatic activity and FSBA binding were abrogated by mutation of both Lys residues, suggesting that either one can bind ATP. Mutation of Glu$^{209}$ (PK catalytic motif III) virtually abrogated kinase activity in the presence of Mg$^{2+}$ or Mn$^{2+}$ ions, suggesting that Glu$^{209}$ functions in ion-dependent PK activity. ICP10 bound the adaptor protein Grb$_2$ in vitro. Mutation of the ICP10 proline-rich motifs at position 396 and 149 reduced Grb$_2$ binding 20- and 2-fold respectively. Binding was abrogated by mutation of both motifs. Grb$_2$ binding to wild type ICP10 was competed by a peptide for the Grb$_2$ C-terminal SH3 motif indicating that it involves the Grb$_2$ C-terminal SH3 (Nelson et al., J. Biol. Chem. 271:17021–17027, 1996).

The construction of the ICP10 PK virus is described by Peng et al. (Virology 216, 184–196, 1996) and Smith et al., (submitted). Briefly, the wild type sequences in a plasmid (TP101) that contains the HSV-2 BamHI E and T fragments were replaced with the 1.8 kb SalI/BglII fragment from pJHL9 [ICP10 mutant deleted in the PK catalytic domain (Luo and Aurelian, J. Biol. Chem. 267:9645–9653, 1992)]. The resulting plasmid, TP9, contains sequences which code for ICP10 deleted in the PK catalytic domain flanked by 4 and 2.8 kb of HSV-2 DNA sequences at the 5' and 3' ends, respectively. The 10 kb HindIII/EcoR1 fragment from TP9 was introduced by marker transfer into a virus (ICP10 RR) in which the RR domain of ICP10 had been replaced with the LacZ gene. The resulting recombinant virus, designated ICP10ΔPK, was obtained by selecting white plaques on a background of blue plaques after staining with X-gal. A few white plaques were picked, purified, and grown in Vero cells with 10% serum (exponentially growing).

There are several known HSV-2 vaccines in the prior art. U.S. Pat. Nos. 4,347,127; 4,452,734; 5,219,567; and 5,171, 568 each teach subunit vaccines which provide some protection against HSV-2 infection. These vaccines are inferior to one in which a live, attenuated virus is used. The immunity induced by a subunit vaccine is restricted to the particular protein represented by the subunit, which may not have sufficient protective potential, Additionally it is non-replicating and there is therefore no amplification of the protein which would further reduce immunogenicity. These problems occur in any sub-unit vaccine regardless of whether the method of preparation is via a recombinant protein or a purification of antigen from a virus.

A cross recombinant vaccine, such as disclosed in U.S. Pat. No. 4,554,159, does not suffer from the problems of the subunit vaccines, but contains the oncogene present in HSV-2. Unless care is taken to define and delete the oncogene, the cross recombinant vaccine would induce cancer in the vaccinee.

The cross recombinant of '159 is temperature sensitive. Avirulence may be obtained by selecting temperature resistance, but the temperature of the mouse is 39° C., while that of a man is 37° C. This temperature sensitivity could well render such a cross problematic in a vaccine. A superior method of selection of avirulence is by the removal of genes coding for virulence without respect to the temperature at which the virus replicates. Also, the use of prototypical crosses would preclude the use of gene deleted or inserted mutants.

Due to the many type-common epitopes on HSV-1 and HSV-2, the antibodies in human serum are cross-reactive (Aurelian, L., Royston, I., and Davis, H. J. Antibody to genital herpes simplex virus: Association with cervical atypia and carcinoma in situ. J. Natl. Cancer Inst. 45:455–464, 1970.) It has also been previously shown that cell-mediated immunity cross-reacts (Jacobs, R. P., Aurelian, L., and Cole, G. A. Cell-mediated immune response to herpes simplex virus: Type specific lymphoproliferative responses in lymph nodes draining the site of primary infection. J. Immunol. 116:1520–1525, 1976).

A live vaccine is superior to a dead vaccine because the live vaccine induces herd immunity; it induces different types of immunity, such as mucosal, cell mediated and humoral immmunity; a higher level of immunity is normally obtained because the virus titers are increased through replication within the vaccinee; and finally a live vaccine is of longer duration, thus obviating boosters and lowering initial dosage. HSV-1 is not as desirable as a candidate for a vaccine against herpes because the major clinical problem is the sexually transmitted HSV-2 which is associated with cancer induction. HSV-1 has a 50% homology with HSV-2, and this may lower the response rate against the heterologous strain in the vaccinated population. All known vaccines for HSV-1 or HSV-2 are cross-reactive and provide complete immunity to the other type. Known vaccines are not type specific. However, an absolute necessity for a live herpes vaccine is the removal of the gene responsible for the association with cancer induction, as in the present invention.

Another absolute requirement for a live vaccine is the absence of lesions upon immunization. A desirable trait in the live vaccine would be its ability to cause a reduction in the frequency of recurrent lesions in a person already infected. There is a substantial population already infected with HSV who may have intercourse with uninfected individuals who would benefit from such a vaccine.

The present invention solves all the problems recited above by providing a whole live attenuated HSV-2 in which the HSV-2 has a deletion of the oncogene, and is formulated in a vaccine composition. The present invention provides a method of immunizing a subject against HSV-1 or HSV-2 with said vaccine composition, providing a superior method of conferring immunity upon the subject.

SUMMARY OF THE INVENTION

It is an object of the present invention to provide a vaccine composition which when administered to an animal, including a human, provides protection from challenge with HSV-2 or HSV-1 infection.

It is a further object of the invention to provide a vaccine composition comprising whole, live, attenuated HSV-2 wherein the oncogene or any portion thereof has been deleted.

It is a further object of the invention to provide a method of immunizing a subject against HSV-2 or HSV-1 comprising administering a novel vaccine composition.

It is even a further object of the present invention to prevent clinical symptoms associated with HSV-2 or HSV-1 comprising administering a novel vaccine composition.

DETAILED DESCRIPTION OF THE INVENTION

Figure 1:
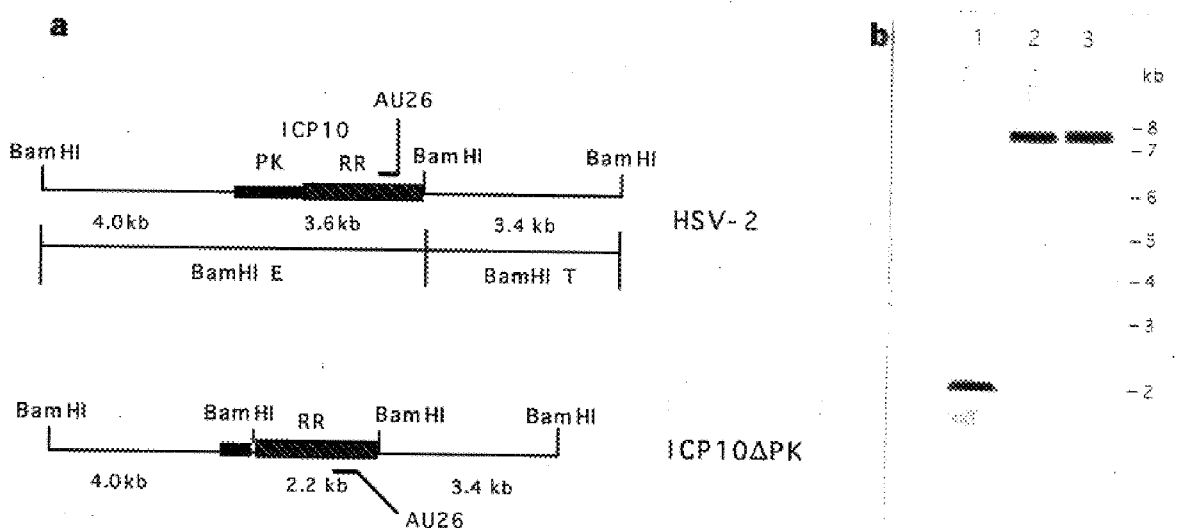
FIG. 1 A. Schematic representation of ICP10ΔPK DNA. Oligoprobe AU26 probe should recognize the 7.6 kb BamHI E fragment from HSV-2 or HSV-2(R) DNA and a 2.2 kb BamHI fragment from ICP10ΔPK DNA. B. Southern blot hybridization of BamH I digested ICP10ΔPK (lane 1), HSV-2 (lane 2), or HSV-2 (R) (lane 3). DNA with the digoxigenin labeled AU26 oligoprobe. Size markers are shown in the right margin.

In the present invention, live whole HSV-2 has been mutated and attenuated to prevent neoplastic transformation. The mutated HSV-2 can be formulated with immune stimulants or adjuvants and used to immunize a subject against HSV-1 or HSV-2. The protein kinase domain of the ribonucleotide reductase (ICP10) has previously been shown to have oncogenic properties. Deletion of the PK domain is shown in the present invention to have deleterious effects on the ability of HSV-2 to infect and transform cells. The present invention demonstrates for the first time that live HSV-2 lacking the PK domain, and hence the oncogene, provides immunogenic protection against challenge with live wild type HSV-2 or HSV-1. Therefore, a novel vaccine composition has been discovered and a novel method of immunizing a subject against HSV-2 or HSV-1.

HSV-1 and HSV-2 viruses are very similar. The DNA is 50% homologous. Virtually all viral proteins have both type-specific and type-common epitopes. For all but 2 protein (i.e for 76 proteins), the type-common epitopes are predominant. The exception is the HSV-2 gG2 (Ashley et al., J. Clin. Invest. 90:511, 1992) and the HSV-2 oncogene which elicit predominantly type-specific antibodies. In the present invention, The HSV-2 oncogene was deleted from ICP10ΔPK. Therefore we only have one protein that can induce type specific immunity. The remaining 76 proteins will induce type common immunity. This includes both antibody and cell mediated immunity.

Previously, live whole HSV-2 could not be explored as a vaccine option for HSV since the oncogene had potential neoplastic implications for the patient. The present invention demonstrates that by removing the oncogene, a protein kinase, from the HSV-2 genome, not only are the neoplastic properties removed, but the virus is attenuated and provides full protection against challenge for an extended period of time.

The particular HSV-2 strain which contains the deleted oncogene is not critical to the present invention. Examples of such strains include HSV-2(G), HSV-2(333), HSV-2 (186), HSV-2(S-1), although any strain is acceptable. These strains are well known and readily available.

The construction of the mutant virus is accomplished by well known techniques. The location of the oncogene (PK) is well-known (DNA Tumor Viruses Oncogenic Mechanisms, Ed. G. Barbanti-Brodano, et al., Plenum Press, NY, 1995, chapter 14 by L. Aurelian, Transformation and Mutagenic Effects Induced by Herpes Simplex Virus Types 1 and 2, p253–280). The oncogene is located in the ICP10 section of the HSV-2 genome. It has previously been shown that the PK activity, and hence oncogenic activity is located at the gene encoding amino acids 1–446. Briefly, the wild type sequences in a plasmid (TP101) that contains the HSV-2 BamHI E and T fragments were replaced with the 1.8 kb SalI/BglII fragment from pJHL9 [ICP10 mutant deleted in the PK catalytic domain (Luo and Aurelian, J. Biol. Chem. 267:9645–9653, 1992)]. The resulting plasmid, TP9, contains sequences which code for ICP10 deleted in the PK catalytic domain flanked by 4 and 2.8 kb of HSV-2 DNA sequences at the 5' and 3' ends, respectively. The 10 kb HindIII/EcoR1 fragment from TP9 was introduced by marker transfer into a virus (ICP10 RR) in which the RR domain of ICP10 had been replaced with the LacZ gene. The resulting recombinant virus, designated ICP10ΔPK, was obtained by selecting white plaques on a background of blue plaques after staining with X-gal. A few white plaques were picked, purified, and grown in Vero cells with 10% serum (exponentially growing).

Southern blot hybridization was used to confirm that the ICP10 PK DNA is deleted in the ICP10 PK coding region. DNA from HSV-2 and ICP10ΔPK was digested with BamH I, separated on 1% agarose gels and transferred to nylon membranes. It was hybridized with the AU26 (CCCCTTCATCATGTTTAAGGA) probe which recognizes a sequence within the ICP10 RR coding region. The hybridizing band seen for ICP10ΔPK DNA was 2.2 kb as compared to 7.6 kb band for wild type HSV-2.

ICP10ΔPK virus can be differentiated from wild type HSV-2 by DNA analysis and immunoprecipitation/immunoblotting with antibody to epitopes located at ICP10 amino acids retained by the deleted protein.

ICP10 PK was precipitated/immunoblotted with anti-LA-1 antibody (recognizes ICP10 amino acids 13–26) (Aurelian, et al., Cancer Cells &:187–191 (1989)) and the proteins were resolved by SDS-PAGE. A 95 kDa protein was recognized by the antibody in cells infected with ICP10ΔPK virus, as compared to the 140 kDa protein from the wild type virus.

The oncogene or any portion thereof may be deleted. By the expression "or any portion thereof" we mean any portion of the oncogene which once deleted results in attenuation of the virus and prevents neoplastic transformation of the cells. Determining if PK activity is absent requires expression of the viral gene and subjecting the result to standard PK assays (Chung et al., 1989). There is abundant guidance in the prior art as to the sections of the ICP10 gene which is required for PK activity. Determining viral attenuation requires testing in animals to determine absence of lesion formation. The techniques for accomplishing this are standard and well-known in the art.

The resultant mutant virus, ICP10ΔPK was used in infection experiments and compared to infections with wild-type HSV-2 and restored HSV-2(R). The cells used in infection are not critical to the present invention. Any human or animal cell line which can be infected with wild type HSV-2 may be used in the present invention. Examples of such cell lines include Vero cells, HeLa cells, 293 cells, or MRC5 cells (all available from American Type Culture Collection). ICP10ΔPK can also be grown in cells that constitutively express ICP10, for example JHLa1. It is titrated by plaque assay on Vero cells with MEM-10% FCS and 0.3% human IgG.

The infection experiments were also conducted in animals. Mice were chosen since mice represent the standard animal model for HSV-2 (M. Wachsman et al, Protection from herpes simplex virus type 2 is associated with T cells involved in delayed type hypersensitivity that recognize glycosylation-related epitopes on glycoprotein D. Vaccine 10:447–454 (1992)). The mouse footpad model was chosen to examine the role of the ICP10ΔPK in viral growth in vivo. Severe lesions were seen in mice given HSV-2, or the restored virus designated HSV-2(R). Mice given ICP10ΔPK had no neurological symptoms nor skin lesions from days 1 through 21.

Immunizing a subject indicates the standard interpretation well known in the art. Upon administration with the vaccine composition, neutralizing antibodies and cell-mediated immunity are raised in the subject and said antibodies and cell-mediated immunity confer immunity to the subject. The latency of the vaccine composition indicates the ability of the vaccine composition to confer immunity over an extended period of time.

The present invention teaches immunization of a subject against HSV-2. A "pfu" is a plaque forming unit and represents the quantity of virus required to form a single plaque when a cell culture is infected with the virus. It is a quantitative measure of viral infectivity used by those skilled in the art. A dose of 500,000 pfu was used to immunize mice. The dosage range for a human is 1 to 100 million pfu. A preferred range is 1000 to 75 million pfu and an especially preferred range is 10,000 to 50 million pfu. Furthermore, due to the 50% homology of HSV-1 and HSV-2 there will be a high degree of protection against HSV-1 infection.

The formulation of ICP10ΔPK for human use is accomplished by suspension in a solution with or without stabilizing ingredients, and with or without immune stimulants and adjuvants. Examples of stabilizing agents, immune stimulants, and adjuvants include alum, incomplete Freud's adjuvant, MR-59 (Chiron), MTPPE, MPL (monophosphoryl Lipid A). Such stabilizing agents, adjuvants and immune stimulants are well known in the art and can be used singly or in combination.

The vaccine composition of the present invention can be adminstered to any animal, including humans. The vaccine composition may be administered via any suitable mode of administration, such as intramuscular, oral, subcutaneous, intravaginal, rectal, or intranasal administration. The preferred mode of administration is subcutaneous administration.

The ICP10ΔPK which provides protection against HSV-2 infection can be administered along with a pharmaceutically acceptable carrier or diluent. Examples of such pharmaceutically acceptable carrier or diluents include water, phosphate buffered saline or sodium bicarbonate buffer. A number of other acceptable carriers or diluents are known.

The following examples are provided for illustrative purposes only and are in way intended to limit the scope of the present invention.

Materials

Cells. Vero (African green monkey kidney) cells were grown in Eagle's minimum essential medium (EMEM) supplemented with 10% fetal calf serum (FCS) and antibiotics. JHLa1 cells (constitutively expresses ICP10) were previously described (Luo and Aurelian, J. Biol. Chem 267:9645–9653, 1992; Smith et al., Virology 200:598–612, 1994; Hunter et al., Virology 210:345–360, 1995). They were cultured in EMEM with 10% FCS, 1 mM Na pyruvate (GIBCO-BRL, Gaithersburg, Md.), 1× non-essential amino acids (GIBCO-BRL) and antibiotics. Vero-ICP10 cells were derived by transfection of Vero cells with an ICP10 expression vector that has a $SV_2$-neo cassette (pJW17N) (Luo and Aurelian, J. Biol. Chem 267:9645–9653, 1992; Smith et al., Virology 200:598–612, 1994). For serum starvation, cells grown to confluency in medium containing 10% FCS, were washed with phosphate-buffered saline (PBS) pH7.0, and grown for two days in medium containing 0.5% FCS.

Plaque forming ability. Virus titers were determined by plaque assay as described (Aurelian, In:Herpes simplex in virus induced immunosuppression, Spector, S., Bendinelli, M. and Freidmen, H., eds. Plenum Press, NY. pp. 73–100, 1989b). Vero-ICP10 cells were used under an overlay consisting of MEM supplemented with 10% or 0.5% FCS and 0.3% IgG.

Antibodies. The production and specificity of the anti-LA-1 antibody specific for ICP10 amino acids 13–26 and monoclonal antibody (MAb 30) that recognizes a determinant in the ICP10 PK domain (amino acids 106–178) were previously described (Aurelian et al., Cancer Cells 7:187–191, 1989a, Chung et al., J. Gen. Virol. 72:1139–1144, 1991). ICP4 and ICP0 MAbs were purchased from Advanced Biotechnologies, (Columbia, Md.). Antibody C-11 to actin was purchased from Santa Cruz Biotechnology (Santa Cruz, Calif.).

Immunofluorescent Staining. Vero cells grown on 22 mm$^2$ glass cover slips (Coming Glass Works, New York) were infected with HSV-2 or ICP10ΔPK and fixed in cold methanol (−70° C.). They were stained (60 min, 37° C.) with anti LA-1 antibody or MAb 30 followed respectively by fluorescein-conjugated goat anti-rabbit or mouse IgG, as described (Wymer et al., J. Virol. 63:277–2784, 1989, Smith et al., Virology 200:598–612, 1994).

EXAMPLE 1

Construction and Characterization of the ICP10ΔPK Virus and HSV-2(R)

The construction of the ICP10ΔPK virus has been described (Peng et al., Virology 216:184–196, 1996). Briefly, the wild type sequences in a plasmid (TP101) that contains the HSV-2 BamHI E and T fragments were replaced with the 1.8 kb SalI/BglII fragment from pJHL9 [ICP10 mutant deleted in the PK catalytic domain (Luo and Aurelian, J. Biol. Chem. 267:9645–9653, 1992)]. The resulting plasmid, TP9, contains sequences which code for ICP10 deleted in the PK catalytic domain flanked by 4 and 2.8 kb of HSV-2 DNA sequences at the 5' and 3' ends, respectively. The 10 kb HindIII/EcoR1 fragment from TP9 was introduced by marker transfer into a virus (ICP10ΔRR) in which the RR domain of ICP10 had been replaced with the LacZ gene. The resulting recombinant virus, designated ICP10ΔPK, was obtained by selecting white plaques on a background of blue plaques after staining with X-gal. A few white plaques were picked, purified, and grown in Vero cells in MEM with 10% FCS (exponential). For the construction of the restored virus HSV-2(R), Vero cells were co-tranfected with 1 µg of infectious viral DNA from ICP10ΔPK and a 10-fold molar excess of the wild type BamHI E/T fragment. A strategy similar to that reported for ICP6Δ (Goldstein and Weller, Virology 166:41–51, 1988b) was used to select restored virus under growth restricted conditions (serum starved Vero cells).

Southern blot hybridization was used to confirm that the ICP10ΔPK DNA is deleted in the ICP10 PK coding region. Generally, viral DNA was isolated from cytoplasmic virions as described (Pignatti et al., Virology 93:260–264, 1979; Smith et al., J. Gen. Virol. 73:1417–1428, 1992a). Briefly, Vero cells were infected at a multiplicity of infection (moi) of 5. At 48 hrs. p.i. cells were resuspended ($2 \times 10^7$ cells/ml) in a buffer consisting of 10 mM Tris-HCl (pH 7.9), 10 mM EDTA and 0.25% Triton. Following incubation on ice (15 min.), NaCl was added at a final concentration of 0.2M and the nuclei were precipitated by centrifugation at 1,000×g (10 min, 4° C.). The supernatant, containing cytoplasmic virions, was incubated in 200 µg/ml Proteinase K and 0.2% SDS (4 hr at 37° C.), mixed with saturated sodium iodide (NaI; final concentration 1.525 g/ml) and ethidium bromide (final concentration 3 µg/ml) and centrifuged at 100,000×g for 16 hrs Viral DNA (15 µg) was digested with BamH I and the fragments were separated by 1% agarose gel electrophoresis in a Tris-Acetate-EDTA (TAE) buffer (40 mM Tris-acetate and 1 mM EDTA). It was transferred to Gene Screen membranes (New England Nuclear Corp.) and the membranes were incubated in a prehybridization solution containing 5×SSC [750 mM NaCl, 75 mM Sodium citrate; pH (7.0)], 2% Casein, 0.1% N-laurylsarcosine and 0.02% sodium dodecyl sulfate (SDS)] at 42° C. for 2 hrs. The hybridization probe was oligonucleotide AU26 (CCCCTTCATCATGTTTAAGGA) (SEQ ID NO. 1) which represents a sequence in the ICP10 RR coding region. It was 3' tailed with Digoxigenin-dUTP (DIG-dUTP) by terminal transferase (Boehringer Mannheim) in 20 µl volume with 1× reaction buffer [5 mM cobalt chloride ($CoCl_2$), 0.05 mM DIG-dUTP, 5 nmol/ml AU26, 0.5 mM dATP and 2.5 units/µl terminal tranferase] at 37° C. for 15 min. diluted to a final concentration of 5 pmol/ml in prehybridization solution. Hybridization was done at 42° C. for 3 hrs. Membranes were washed once (room temperature) in a solution containing 2×SSC, 0.1% SDS for 5 mins and twice in 0.5×SSC, 0.1% SDS for 15 mins. For detection of the hybridized DNA fragments, the membranes were rinsed in Buffer 1 (100 mM Tris-HCl, pH 7.5, 150 mM NaCl), incubated in Buffer 2 [2% (w/v) casein in Buffer 1] for 40 min and in Buffer 2 containing $3 \times 10^{-4}$ U/ml of alkaline phosphatase-conjugated anti-digoxigenin antibody (Boehringer Mannheim) for 30 min. After washing with Buffer 1 (twice) and soaking in Buffer 3 (100 mM Tris-HCl, pH 9.5, 100 mM NaCl, 50 mM $MgCl_2$) for 2 min, the membranes were exposed to the chemiluminescent substrate Lumi-Phos™ 530 (Boehringer Mannheim) and the reaction was developed on X-ray film.

More specifically, DNA (15 µg) from HSV-2, ICP10ΔPK or HSV-2(R) was digested with BamHI, separated on 1% agarose gels and transferred to nylon membranes. It was hybridized with the AU26 probe which recognizes a sequence within the ICP10 RR coding region (FIG. 1A). A hybridizing 7.6 kb band which represents the BamHI E fragment was observed for HSV-2, (FIG. 1B, lane 2) and HSV-2(R) (FIG. 1B, lane 3) DNA. The hybridizing band seen for ICP10ΔPK DNA was 2.2 kb (FIG. 1B, lane 1) consistent with the expected size. The data confirm that ICP10ΔPK DNA is deleted in the PK coding region.

EXAMPLE 2

Expression of the 95 kDa PK deleted ICP10 protein (p95)

To determine whether ICP10ΔPK expresses an ICP10 protein deleted in its PK domain, Vero cells were infected with ICP10ΔPK (200 pfu/cell) and labeled with [$^{35}$S]-methionine (100 µCi/ml) from 6–16 hrs p.i. Cells infected with HSV-2 or HSV-2(R) served as controls. Generally, cells were mock-infected with PBS (pH7.4) or infected with 200 PFU/cell of HSV-2, ICP10ΔPK, or HSV-2 (R). They were labeled with [$^{35}$S] methionine (100 µCi/ml) (sp Act 1120 Ci/mmol, Dupont, NEN Research Products) in EMEM containing no methionine and 10% dialyzed FCS. In some experiments, infection was done in the presence of cycloheximide (50 µg/ml) for 6 hr at which time cycloheximide was removed, cells were washed extensively with PBS, and incubated (3 hrs) in the presence of 10 µg/ml actinomycin D and 100 µCi/ml of [$^{35}$S]-methionine. For immunoprecipitation, cell lysates were incubated in cold RIPA buffer [0.01M Tris-HCl (pH 8.0), 0.1% SDS, 1% Nonidet P-40, 1% deoxycholate, 0.15M NaCl, 1 mM dithiothreitol] with 1 mM phenylmethylsurfonyl fluoride (PMSF), 100 Kallikrein units/ml aprotinin (Sigma) for 15 min on ice, and cleared of cell debris by centrifugation for 30 min at 20,000×g. They were incubated with 15–20 µl of antibody (1 hr, 4° C.) and 100 µl protein A-Sepharose CL4B beads [10 mg in 0.1M Tris-HCl (pH 8.0), 0.15M NaCl and 0.5% Nonidet P-40] (30 mins, 4° C.). Beads were washed extensively with ice-cold RIPA buffer, and bound proteins were eluted by boiling (5 min) in 100 µl denaturing solution [150 mM Tris hydrochloride (pH 7.0), 5.7% SDS, 14% 2-mercaptoethanol, 17% sucrose and 0.04% bromothymol blue].

Proteins were resolved by SDS-PAGE on 7% or 8.5% polyacrylamide gels and visualized by autoradiography. In some experiments, cells were resuspended directly into denaturing solution, boiled for 5 min., and analyzed by SDS-PAGE.

Figure 2:
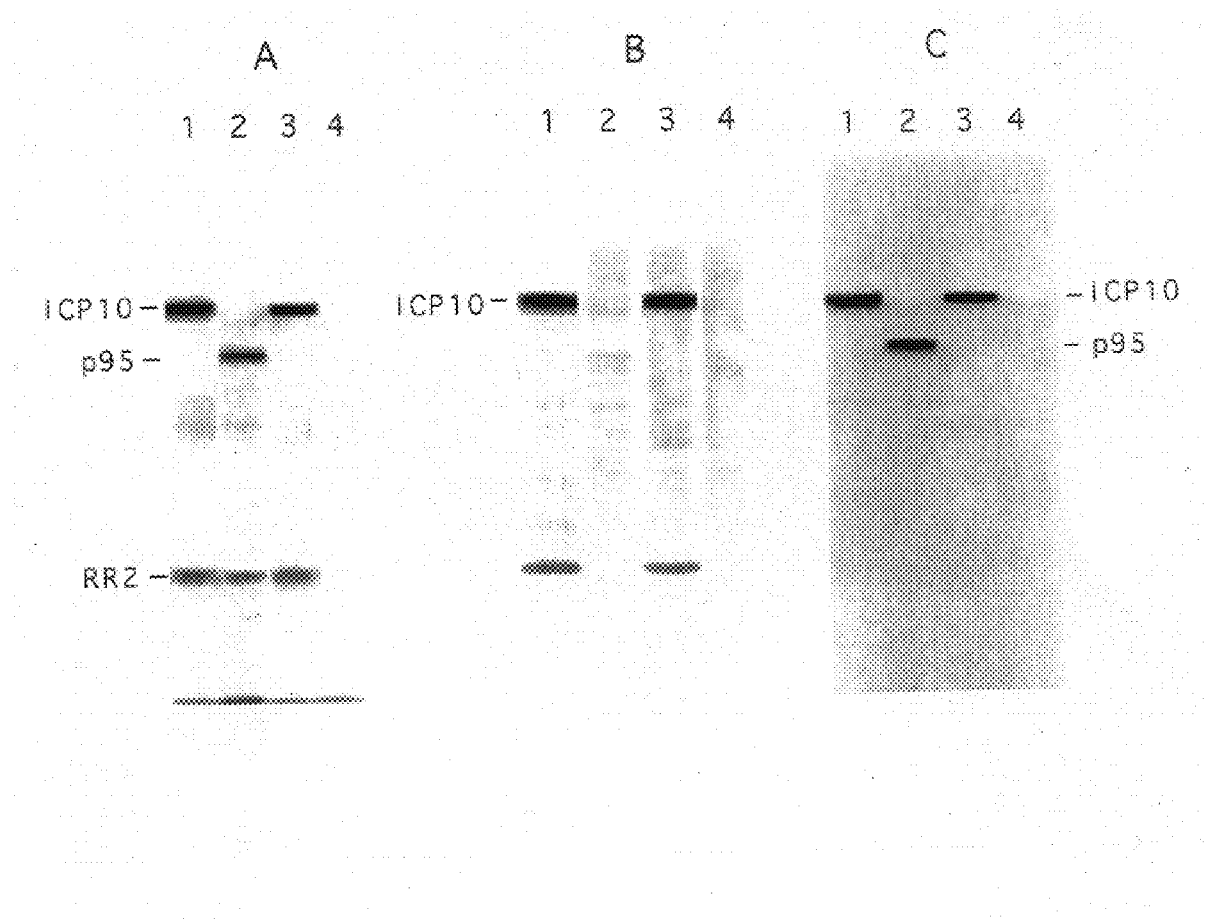
FIG. 2 Expression and PK activity of the p95 protein from ICP10ΔPK infected cells. A. Vero cells were infected with HSV-2 (lanes 1,4), ICP10ΔPK (lane 2), or HSV-2 (R) (lane 3), labeled with [$^{35}$S]-methione from 6–16 hrs p.i. and extracts immunoprecipitated with anti LA-1 antibody (lanes 1–3) or preimmune serum (lane 4). B. Immunocomplex PK assays with anti LA-1 antibody (lanes 1–3) or preimmune serum (lane 4) of extracts from Vero cells infected for 16 hrs with HSV-2 (lane 1,4), ICP10ΔPK (lane 2) or HSV-2(R) (lane 3). C. The immunoprecipitates in Panel B were immunoblotted with anti LA-1 antibody.

More specifically, cell extracts were precipitated with anti-LA-1 antibody and the proteins were resolved by SDS-PAGE on 7% polyacrylamide gels. Anti-LA-1 antibody precipitated a 140 kDa protein from HSV-2 (FIG. 2A, lane 1) or HSV-2(R) (FIG. 2A, lane 3) infected cells. From ICP10ΔPK infected cells, it precipitated a 95 kDa protein (p95) (FIG. 2A, lane 2) which is consistent with the PK deleted ICP10 (Luo and Aurelian, J. Biol. Chem. 267:9645–9653, 1992) . The preimmune serum was negative (FIG. 2A, lane 4). A 38 kDa protein consistent with RR2 was co-precipitated by anti-LA-1 antibody from cells infected with all three viruses, indicating that p95 can complex with RR2, presumably at the carboxy terminus previously implicated in complex formation (Chung et al., J. Gen. Virol. 72:1139–1144, 1991).

EXAMPLE 3 p95 expressed by ICP10ΔPK lacks kinase activity

We have previously shown that: (i) ICP10 has kinase activity in HSV-2 infected and stably transfected cells, and (ii) PK activity is associated with the 57–60 kDa amino terminal domain of the ICP10 protein, but not with its 90–95 kDa carboxy terminal domain (Chung et al., J. Virol. 63:3389–3398, 1989; Smith et al., Virology 200:598–612, 1994). To determine whether p95 expressed by ICP10ΔPK has PK activity, extracts of cells infected with HSV-2, ICP10ΔPK or HSV-2(R) (moi=200, 16 hrs p.i.) were immunoprecipitated with anti-LA-1 antibody and subjected to PK assays (Chung et al., J. Virol. 63:3389–3398, 1989).

Generally, immunoprecipitates of cell extracts normalized for protein concentration by the BCA protein assay kit, (PIERCE, Rockford, Ill.) were washed with TS buffer containing 20 mM Tris-HCl (pH 7.4), 0.15M NaCl, suspended in 50 μl of kinase reaction buffer consisting of 20 mM Tris-HCl (pH 7.4), 5 mM $MgCl_2$, 2 mM $MnCl_2$ and 10 μCi of [$-^{32}p$] ATP (3000 Ci/mmol, Dupont, New England Research Product), and incubated at 30° C. for 15 min (Chung et al., J. Virol. 63:3389–3398, 1989; Chung et al., Virology 179:168–178, 1990; Smith et al., J. Gen. Virol. 73:1417–1428, 1992; Smith et al., Virology 200:598–612, 1994; Peng et al., Virology 216:184–196, 1996). The beads were washed once with 1 ml TS buffer, resuspended in 100 μl of denaturing solution and boiled for 5 min. The proteins were resolved by SDS-PAGE on 7% polyacrylamide gels as described (Chung, et al., J. Virol. 63:3389–3398, 1989). Proteins were electrotransferred onto nitrocellulose membranes as previously described (Aurelian et al., Cancer Cells 7:187–191, 1989a) and immunoblotting was performed by incubation with the respective antibodies followed by protein A-peroxidase (Sigma) for 1 hr at room temperature each. Detection was with ECL reagents (Amersham, Chicago, Ill.), as described (Smith et al., Virology 200:598–612, 1994).

More specifically, the resolved proteins were transferred to a nitrocellulose membrane and immunoblotted with anti-LA1 antibody to determine the levels of protein in the precipitates. The 140 kDa ICP10 protein from HSV-2 (FIG. 2B, lane 1) or HSV-2(R) (FIG. 2B, lane 3) infected cells was phosphorylated. A phosphorylated 95 kDa protein was not seen in cells infected with ICP10ΔPK (FIG. 2B, lane 2). This is not due to low levels of protein in the precipitates used for PK assay, because similar protein levels were seen for all three viruses by immunoblotting with anti LA-1 antibody (FIG. 2C). A phosphorylated 38 kDa protein was seen in HSV-2 (FIG. 2B, lane 1) and HSV-2(R) (FIG. 2B, lane 3) infected cells but not in cells infected with ICP10ΔPK (FIG. 2B, lane 2). Preimmune serum was negative (FIG. 2B,C, lane 4). We interpret these data to indicate that RR2 is phosphorylated by ICP10 PK, as previously reported by Chung et al., J. Virol. 63:3389–3398, 1989 and Peng et al., Virology 216:184–196, 1996. It is not phosphorylated by p95, consistent with the absence of the PK domain. The data confirm that the ICP10 PK coding region is required for kinase activity also within the context of virus infection.

EXAMPLE 4

Ribonucleotide reductase activity of ICP10ΔPK

It is generally believed that the RR and PK activities of the RR1 protein can be dissociated (Ingemarson et al., Virology 156:417–422, 1987; Chung et al., J. Virolo. 63:3389–3398, 1989). To examine the validity of this interpretation it is important to document whether the loss of ICP10 PK activity has any effect on RR activity. RR assays were performed on extracts from infected cells (moi=20, 16 hrs, p.i.). Generally, RR activity was assayed as described (Smith et al., J. Gen Virol. 73:1417–1428, 1992). Extracts from 16 hrs infected cells or mock infected cells were resuspended in HD buffer [100 mM HEPES buffer (pH 7.6), 2 mM dithiothreitol (DTT)] at $2×10^7$ cell equivalents/ml, incubated on ice for 15 mins, disrupted by sonication (30–60 secs at maximum setting; Ultrasonics model 220F Sonifier) and clarified of cell debris by centrifugation (100,000×g; 1 hr, 4° C.). The HSV RR activity was precipitated with crystalline ammonium sulfate [45% saturation (0.258 g/ml)]. Following dialysis and centrifugation (16,000×g; 30 min), the partially purified enzyme preparations were incubated (37° C.; 10 min) with equal volumes of a 2× standard reaction mixture containing 400 mM HEPES buffer (pH 8.0), 20 mM DTT and 0.2 mM [$^3$H]-CDP (17.8 Ci/mmol, Amersham, Ill.). The reaction was terminated by the addition of 100 mM hydroxyurea with 10 mM EDTA (pH 8.0) and boiling for 3 min. *Crotalux atrox* venom (Sigma, St. Louis, Mo.) was added [0.5 mg/ml in 12 mM Tris-HCl (pH 9.0), 4 mM $MgCl_2$, 1 mM deoxycytidine) and the mixture was incubated 30 min at 37° C., boiled for 3 min and applied to a 0.5 ml Dowex-1 borate column (Sigma). The column was washed with 2.5 ml $H_2O$ and 0.5 ml eluate fractions were mixed with Biofluor (New England Nuclear, Boston, Mass.) for scintillation counting. Ribonucleotide reductase activity is expressed as units/mg, where 1 unit represents the conversion of 1 nmol [$^3$H]-CDP to dCDP/hr/mg protein.

More specifically, as shown in Table 1, the ICP10ΔPK virus had a similar RR activity as that of HSV-2 and HSV-2(R). This is consistent with the finding that p95 coprecipitates with RR2 and suggests the conclusion that the PK and RR activities can be functionally dissociated.

EXAMPLE 5

Growth properties of ICP10ΔPK

Figure 3:
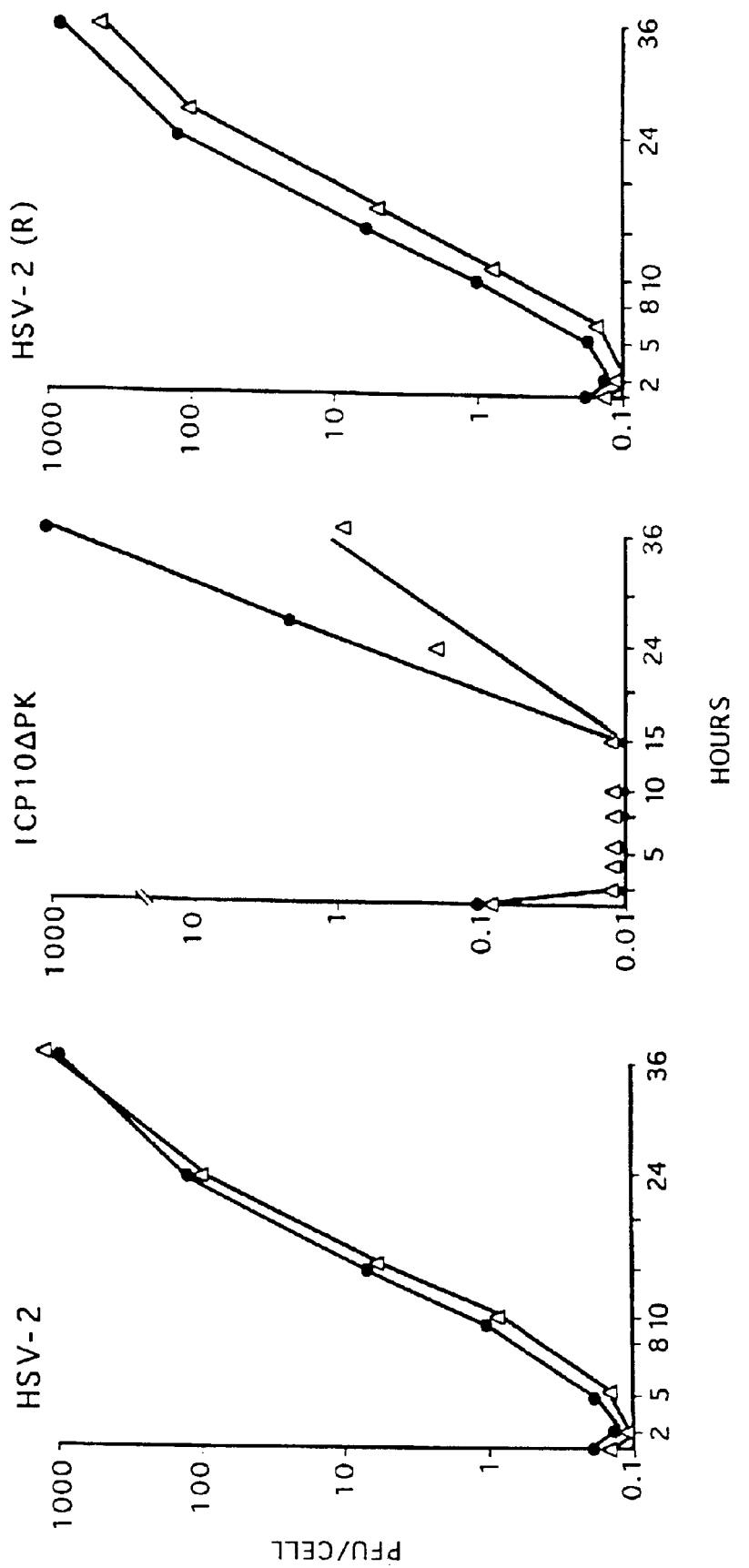
FIG. 3 Virus growth under exponential and growth restricted conditions. Vero cells grown in 10% serum (•) or 0.5% serum (Δ) were infected with HSV-2 (A), ICP10ΔPK (B), or HSV-2(R) (C) at an moi of 2. Virus titers were assayed at 2 to 36 hrs. p.i. Results are expressed as PFU/cell (burst size).

The growth properties of ICP10ΔPK were studied under exponential (10% serum) and growth restricted (0.5% serum) conditions. In a first series of experiments, Vero cells were infected with HSV-2, ICP10ΔPK, or HSV-2(R) at moi of 2 and virus growth examined for 36 hrs p.i. As shown in FIG. 3, HSV-2 grew equally well under exponential and growth restricted conditions. Virus replication began at 2 hr p.i. and reached peak levels at 36 hrs p.i. (burst size 1000 pfu/cell). A similar growth pattern was evidenced by HSV-2(R) (FIG. 3C). By contrast, onset of ICP10ΔPK replication was not seen until 15 hrs p.i. both in exponential and serum starved cells. At that time replication resumed, reaching titers similar to those of HSV-2 at 36 hrs p.i. in exponential cells (burst size 1000 pfu/cell), but not in serum starved cells (burst size 1 pfu/cell) (FIG. 3B).

Figure 4:
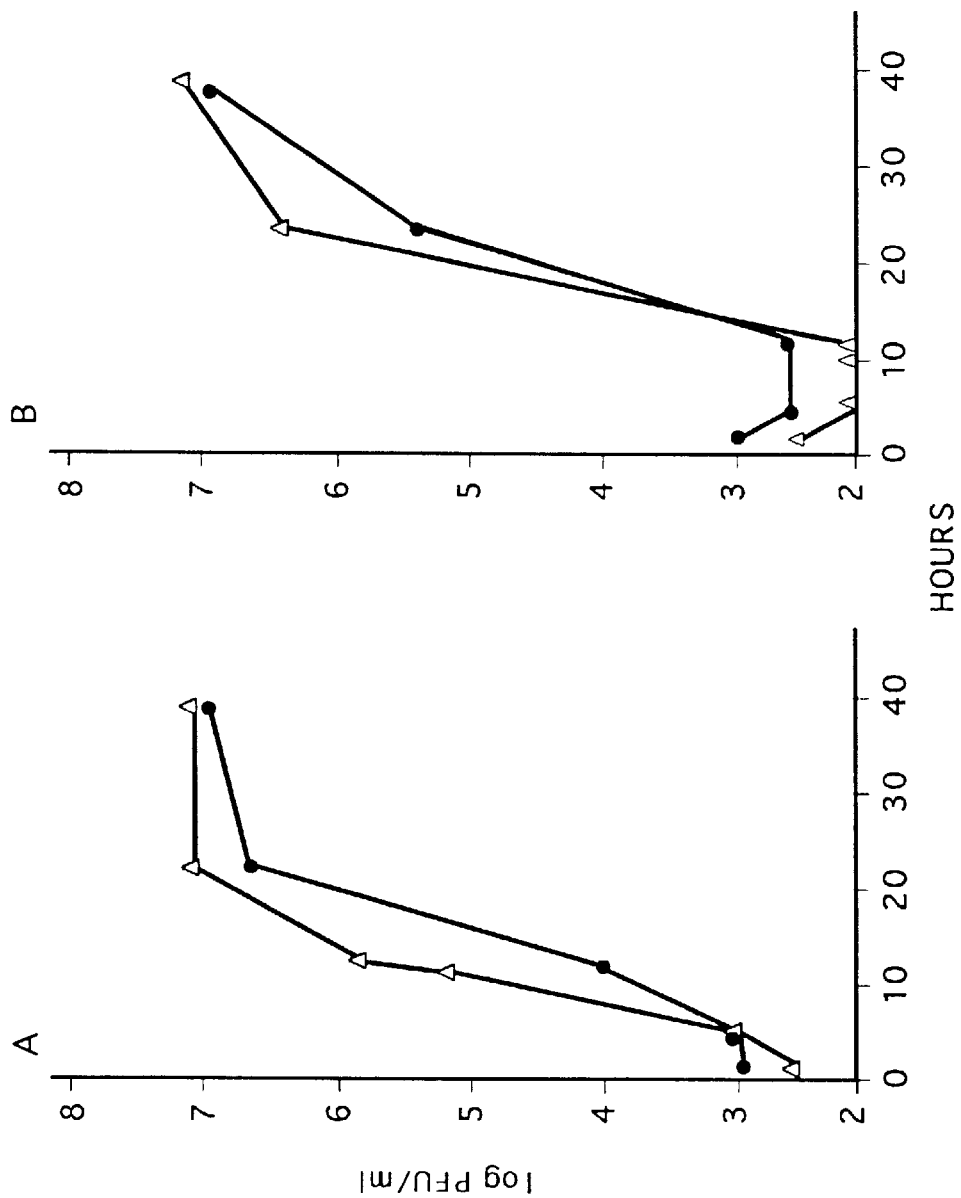
FIG. 4 Extracellular and intracellular virus titers in Vero cells infected at a high moi. Exponential Vero cells were infected with HSV-2 (A) or ICP10ΔPK (B) at an moi of 200 and intracellular (Δ) and extracellular (•) virus titers were determined at 2 to 36 hrs. p.i.

In a second series of experiments, exponential Vero cells were infected with HSV-2, or ICP10ΔPK at moi of 200. HSV-2 replication began at 2 hrs p.i. and reached maximal titers at 20 hrs p.i. (FIG. 4A). By contrast, replication of ICP10ΔPK virus was first seen at 12 hrs p.i., with maximal titers at 36 hrs p.i. (FIG. 4B). The growth of HSV-2(R) was virtually identical to that of HSV-2 (data not shown). The titers of intracellular and extracellular virus were similar for HSV-2, ICP10ΔPK and HSV-2(R), indicating that progeny virus was released as well as HSV-2 (FIG. 4).

Figure 5:
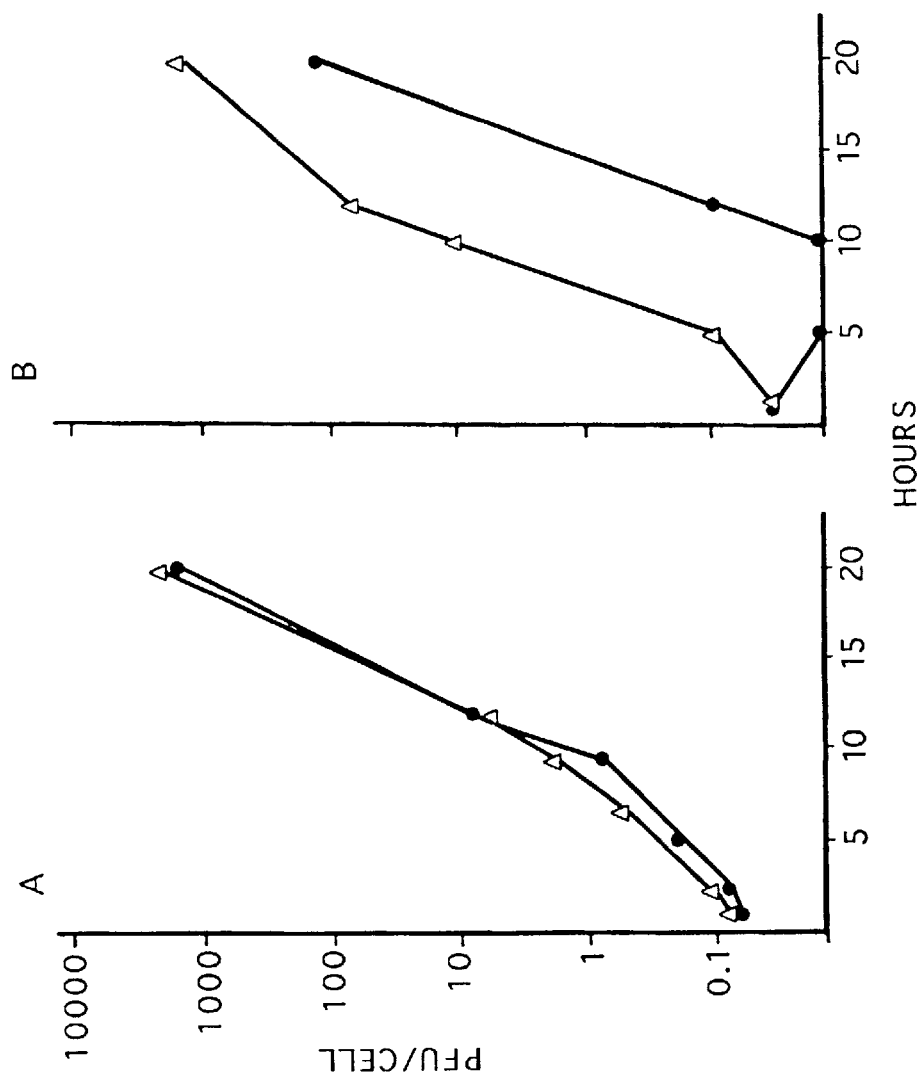
FIG. 5 ICP10ΔPK virus growth in cells that constitutively express ICP10. JHLa1 cells, that constitutively express ICP10 (A) or 293 cells, that were used to establish the JHLA1 line (B), were infected with HSV-2 (Δ) or ICP10ΔPK (•) at an moi of 200. Virus titers were assayed at 2 to 20 hrs p.i. Results are expressed as PFU/cell (burst size).

To confirm that ICP10 PK is indeed required for virus replication we also examined virus growth in JHLa1 cells that constitutively express ICP10. 293 cells which were used to establish the JHLa1 line were used as control (Luo and Aurelian, J. Biol. Chem 267:9645–9653, 1992; Smith et al., Virology 200:598–612, 1994; Hunter et al., Virology 210:345–360, 1995). Cells were infected at moi of 200 and overlayed with MEM-1% FCS. ICP10ΔPK growth in 293 cells was similar to that seen in Vero cells in that newly synthesized virus was not seen before 10 hrs p.i. (FIG. 5B). By contrast, in JHLa1 cells, ICP10ΔPK grew as well as HSV-2 with replication first seen at 2 hrs p.i. and reaching maximal levels at 20 hrs p.i. (burst size; 2800 and 2500 for HSV-2 and ICP10ΔPK respectively) (FIG. 5A). We interpret these findings to indicate that ICP10 PK is required for virus replication both in exponential and growth restricted cells. However a compensatory function(s) seen in both Vero and 293 cells is responsible for the resumption of virus growth at 10–15 hrs p.i. Because the growth of ICP10ΔPK virus resumed earlier in cells infected at high moi (10–12 hrs p.i.) than low (15 hrs p.i.) moi, but the burst size was significantly higher in exponential than in serum starved cells (1000 vs 1 respectively) we assume that the compensatory function is a cellular Ser/Thr PK induced by incoming virus structural protein(s).

EXAMPLE 6

ICP10ΔPK and HSV-2 have similar cell adsorption kinetics

Figure 6:
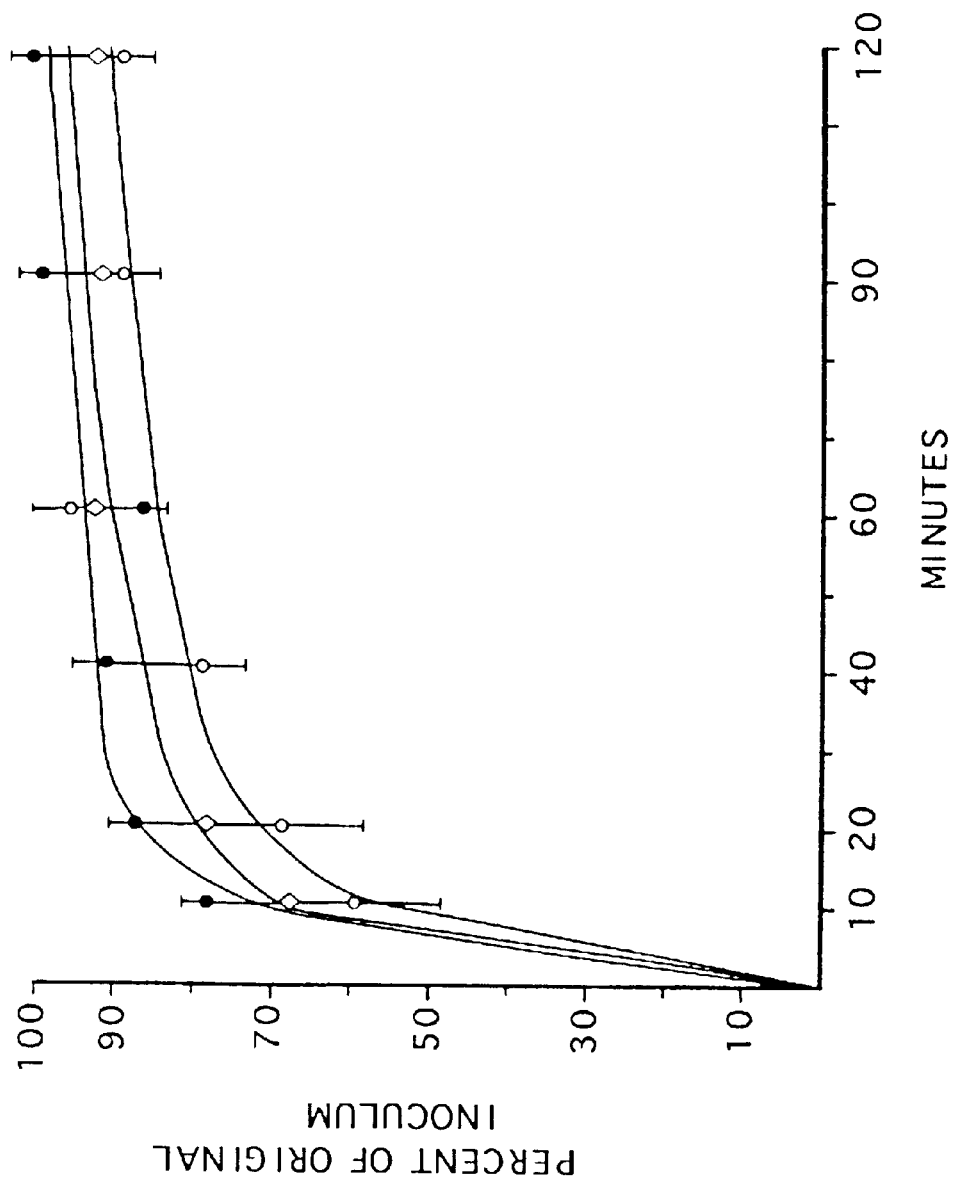
FIG. 6 Adsorption/penetration kinetics of ICP10ΔPK. Vero cells were exposed to 200 pfu of HSV-2 (•), ICP10ΔPK (o) or HSV-2 (R) (◇) for 0, 10, 30, 60, 90, 120 min., overlayed with MEM 10% serum and 0.3% IgG, reincubated at 37° C. for 48 hrs and scored for plaque formation. Data are presented as the % of the original inoculum.

One possible interpretation for the growth pattern evidenced by ICP10ΔPK is that it is defective in its ability to adsorb/penetrate the cells. To address this question, Vero cells were exposed to 200 pfu of HSV-2, ICP10ΔPK, or HSV-2(R) for 0, 10, 30, 60, 90 or 120 minutes. They were extensively washed with PBS, overlayed with MEM-10% FCS and 0.3% IgG and re-incubated at 37° C. for 48 hrs. At this time they were scored for plaque formation. As shown in FIG. 6, the number of plaques increased for all three viruses as a function of exposure time, reaching maximal levels at 20–30 min. and plateauing thereafter. Virus titers in the original inocula decreased in parallel, with similar patterns seen for HSV-2, ICP10ΔPK, and HSV-2(R) (data not shown).

EXAMPLE 7

Plaque forming ability of ICP10ΔPK virus

Figure 7A:
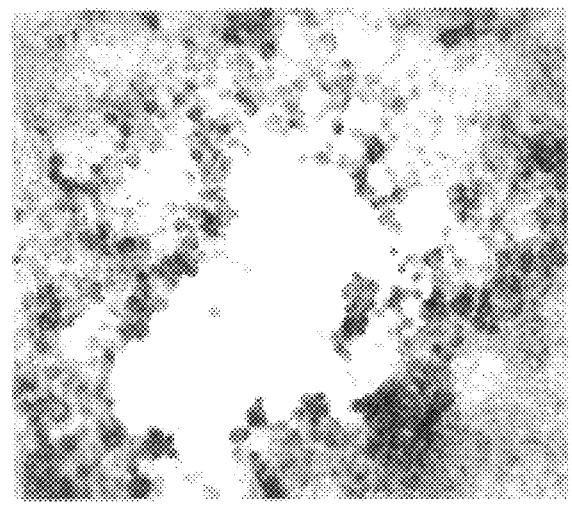
FIG. 7 Plaques in Vero cells. Cells were infected with HSV-2 (A) or ICP10ΔPK (B) under an overlay consisting of MEM-10% FCS and 0.3% IgG. (Giemsa stain).
Figure 7B:
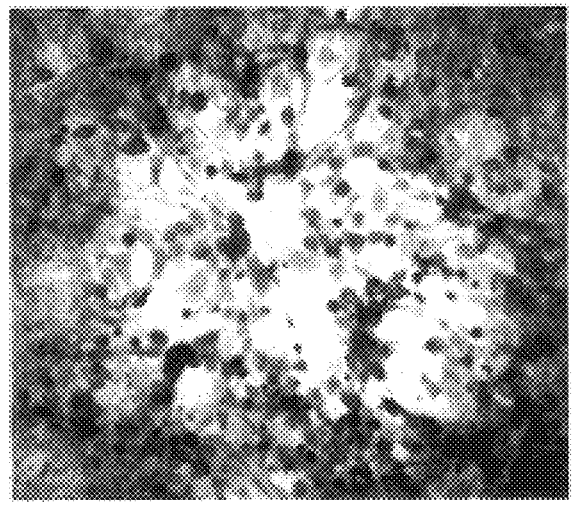

To analyze the plaque forming ability of ICP10ΔPK we used Vero and Vero-ICP10 cells grown in 10% or 0.5% serum. Consistent with the low burst size observed in serum starved cells infected at low moi, ICP10ΔPK plaque forming ability was severely compromised in serum-starved Vero cells. Virus titers were similar to those of HSV-2 in exponential growing Vero cells (10% serum) and in Vero-ICP10 cells (Table 2). In Vero cells (grown in 10% or 0.5% FCS), ICP10ΔPK plaques were hazy, apparently reflecting incomplete cell lysis (FIG. 7B). The extent of cell lysis differed somewhat from one experiment to the next, but it was never as complete as that seen for HSV-2 (FIG. 7A). The morphology of the ICP10ΔPK plaques in Vero-ICP10 cells and that of HSV-2 (R) plaques in all cells was similar to that of HSV-2 (data not shown).

EXAMPLE 8

Figure 8:
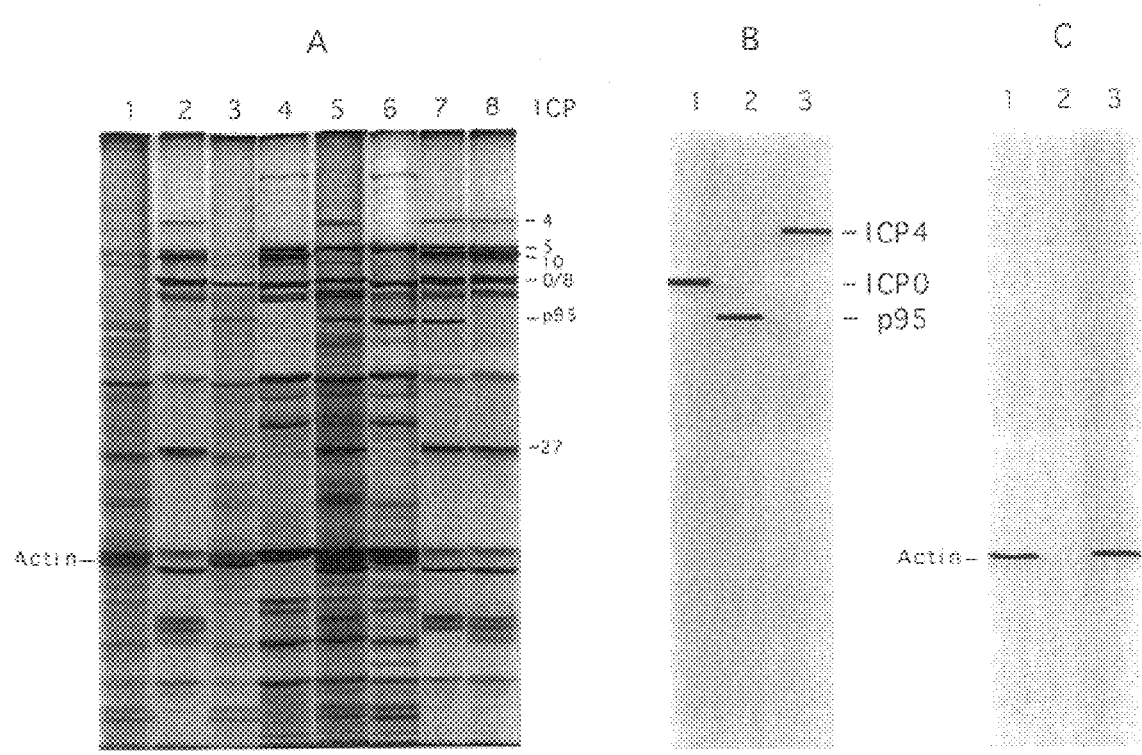
FIG. 8 Protein profiles of HSV-2 and ICP1Δ10PK infected cells. A. Vero cells (lanes 1–6, 8) were mock infeced (lane 1) or infected with HSV-2 (lanes 2, 4), ICP10ΔPK (lanes 3, 5, 6,) or HSV-2 (R) (lane 8) and labeled with [$^{35}$S]-methionine from 2–3 hrs p.i., (lanes 1–3, 8), 7–8 hrs p.i. (lanes 4, 5), or 11–12 hrs p.i. (lane 6). The protein profile in JHLa1 cells (constitutively express ICP10) infected with ICP10ΔPK, and labeled with [$^{35}$S]-methionine from 2–3 hrs p.i served as control (lane 7). Proteins from cell extracts were resolved by PAGE on 8.5% SDS acrylamide gels. B. Extracts of cells infected with ICP10ΔPK for 3 hrs (lanes 1,2 ) or 8 hrs p.i. (lane 3) were immunoblotted with ICP0 MAb (lane 1), anti LA-1 antibody (lane 2) or ICP4 MAb (lane 3). C. Extracts of Vero cells mock infected (lane 1), infected with HSV-2 for 3 hrs (lane 2) or ICP10ΔPK for 12 hrs. were immunoblotted with antibody to actin.

IE protein expression is inhibited in ICP10ΔPK infected cells early in infection The growth defect of ICP10ΔPK virus may reflect its failure to initiate protein synthesis. To address this possibility, Vero cells were mock infected or infected with HSV-2, ICP10ΔPK, or HSV-2(R) (moi=200) for 2 or 7 hrs, pulse labeled with [$^{35}$S]-methionine for an additional 60 min., and proteins were resolved by SDS-PAGE. The protein profiles in HSV-2 infected cells were similar to those previously described (Wilcox et al., J. Virol. 33:167–182, 1980) and included, at 3 hrs p.i., ICP4, ICP0, ICP10, and ICP27 (FIG. 8A, lane 2). Similar protein profiles were seen in cells infected with HSV-2(R) (FIG. 8A, lane 8). By contrast, the protein profiles in cells infected with ICP10ΔPK for 3 hrs (FIG. 8A, lane 3) resembled those in mock infected cells (FIG. 8A, lane 1). The exception were two bands, 110 kDa and 95 kDa (FIG. 8A, lane 3) which were respectively recognized by ICP0 and ICP10 antibodies in immunoblotting (FIG. 8B, lanes 1,2). Densitometric scanning indicated that the levels of ICP0 were 4-fold lower in ICP10ΔPK than HSV-2 [or HSV-2(R)] infected cells (3130 and 782 units for HSV-2 and ICP10ΔPK respectively) and the p95 levels (in ICP10ΔPK infected cells) were 7-fold lower than the ICP10 levels [in HSV-2 and HSV-2(R) infected cells] (3567 and 480 units for ICP10 and p95 respectively). In cells infected with ICP10ΔPK for 8 hrs, the levels of ICP0 and p95 were higher, and bands consistent with ICP4, ICP5, and ICP27 were detected (FIG. 8A, lane 5). The identity of the ICP4 band in 8 hrs infected cells was confirmed by immunoblotting with ICP4-specific MAb (FIG. 8B, lane 3). The protein profile in ICP10ΔPK infected cells at 12 hrs p.i. (FIG. 8A, lane 6) was similar to that of HSV-2 infected cells at 8 hrs p.i. (FIG. 8A, lane 4). These findings indicate that viral proteins other than ICP0 and p95 are not expresed in cells infected with ICP10ΔPK for 3 hrs suggesting that ICP10 PK is required for expression of IE proteins ICP4, ICP22 and ICP27. Indeed the protein profile in ICP10ΔPK infected JHLa1 cells (supply ICP10 PK activity) at 3 hrs p.i. is virtually identical to that of HSV-2 infected cells (FIG. 8A, lane 7). Because these three IE proteins are responsible for the regulation of early and late viral gene expression (Sacks et al., J. Virol. 55:796–805, 1985; McCarthy et al., J. Virol. 63:18–27, 1989; Samaniego et al., J. Virol. 69:5705–5715, 1995; Dixon and Schaffer, J. Virol. 36:189–203, 1980; Rice et al., J. Virol. 69:5550–5559, 1995; Leopardi and Roizman, Proc. Natl. Acad. Sci. U.S.A. 93:4562–4576, 1996), their absence from ICP10ΔPK infected cells result in complete inhibition of viral protein synthesis and infectious virus production.

Figure 9:
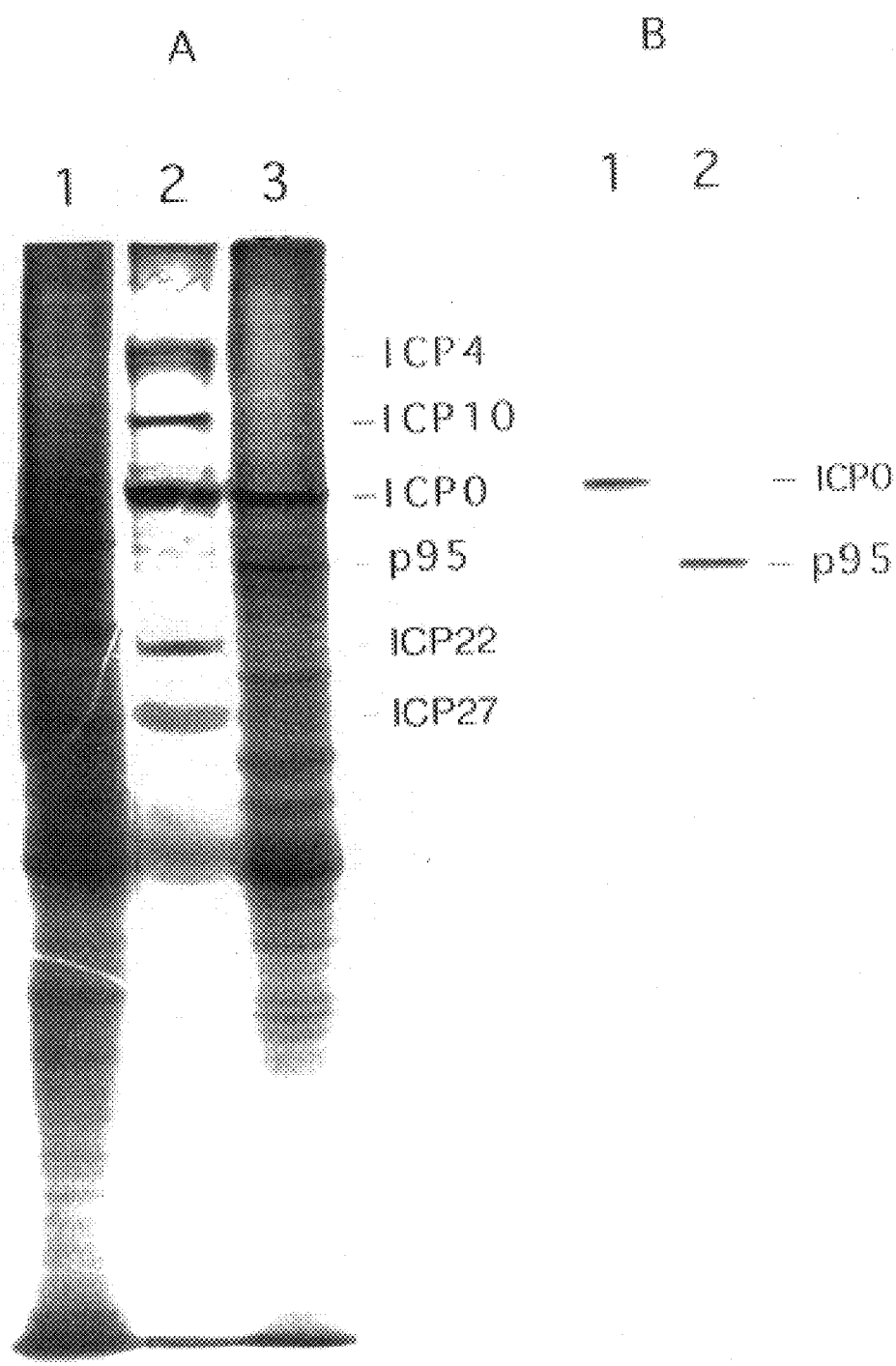
FIG. 9 IE protein synthesis in HSV-2 and ICP10ΔPK infected cells. A. Vero cells were mock infected (lane 1) or infected with HSV-2 (lane 2) or ICP10ΔPK in the presence of 50 μg/ml cycloheximide (6 hrs) and labeled with [$^{35}$S]-methionine for 3 hrs in medium containing 10 μg/ml actinomycin D. Proteins were resolved by PAGE on 8.5% acrylamide gels. B. Immunoblotting of extracts in lanes 2,3 in panel A with ICP0 MAb (lane 1) and anti-LA-1 (lane 2).

To further examine the synthesis of IE proteins in ICP10ΔPK infected cells, infection was done in the presence of 50 µg/ml cycloheximide (6 hr) and cells were labeled with [$^{35}$S]-methionine for 3 hrs in medium containing 10 µg/ml of actinomycin D, conditions that allow IE gene expression, but not expression of other viral genes (Honess and Roizman, J. Virol. 14:8–19, 1974; Strnad and Aurelian, Virology 73:244–258, 1976). Proteins consistent with ICP4, ICP10, ICP0, ICP22, and ICP27 were seen in HSV-2 infected cells (FIG. 9A, lane 2). By contrast, ICP4, ICP10, ICP22 and ICP27 were not seen in ICP10ΔPK infected cells (FIG. 9A, lane 3). A 110 kDa protein, consistent with ICP0, and a 95 kDa protein, consistent with p95, were seen in ICP10ΔPK infected cells (FIG. 9A, lane 3), but their levels were respectively 2-fold and 3-fold lower than in HSV-2 infected cells (FIG. 9A, lane 2) (densitometric integration units 1760 and 3520 for ICP0; 733 and 2200 for p95 and ICP10, in ICP10ΔPK and HSV-2 infected cells, respectively). Immunoblotting confirmed that the 110 kDa and 95 kDa proteins were ICP0 and p95 respectively (FIG. 9B, lanes 1,2). The protein profiles for HSV-2(R) were similar to those for HSV-2 (data not shown). These data support the conclusion that ICP10 PK is required for expression of ICP4, ICP22, and ICP27, but not ICP0 and p95.

EXAMPLE 9

ICP4 mRNA is not seen at 3 hrs p.i. with ICP10ΔPK

To examine whether the failure to detect ICP4 protein in cells infected with ICP10ΔPK for 3 hrs reflects a transcriptional defect, we used Northern blot hybridization with RNA from Vero cells infected with HSV-2, ICP10ΔPK, or HSV-2(R) and ICP4 DNA as probe. Generally, the guanidium isothiocyanate/cesium chloride gradient method was used to isolate and purify RNA from Vero cells infected with HSV-2, ICP10ΔPK or HSV-2(R) (moi=200) for 4 hrs p.i. Northern blot hybridization was done as described (Feng et al., Antisense Nucleic Acid Development 6:25–35, 1996). Hybridization was for 16 hrs at 42° C. with [$^{32}$P]-labeled ICP4 or ICP0 DNA probes in a solution containing 40% formamide, 6×SSPE, 2×Denhardt's, 0.1% SDS, and 250 μg/ml salmon sperm DNA. The ICP4 probe was a 1.9 kb BamHI DNA fragment derived from pXhoI-C. The ICP0 probe was a 1.7 kb NruI-SalI fragment derived from pIGA15 (O'Hare and Hayward, J. Virol. 53:751–760, 1985). The probes were [$^{32}$P]-dCTP labeled by the random priming method using an oligonucleotide kit (Pharmacia, Uppsala, Sweden) according to manufacturer's instructions. Blots were washed twice in 2×SSC-0.1% SDS and twice in 0.1×SSC-0.01% SDS for 10 min. each at ambient temperature followed by one wash in 0.1×SSC-0.1% at 50° C. and visualized by autoradiography.

Figure 10:
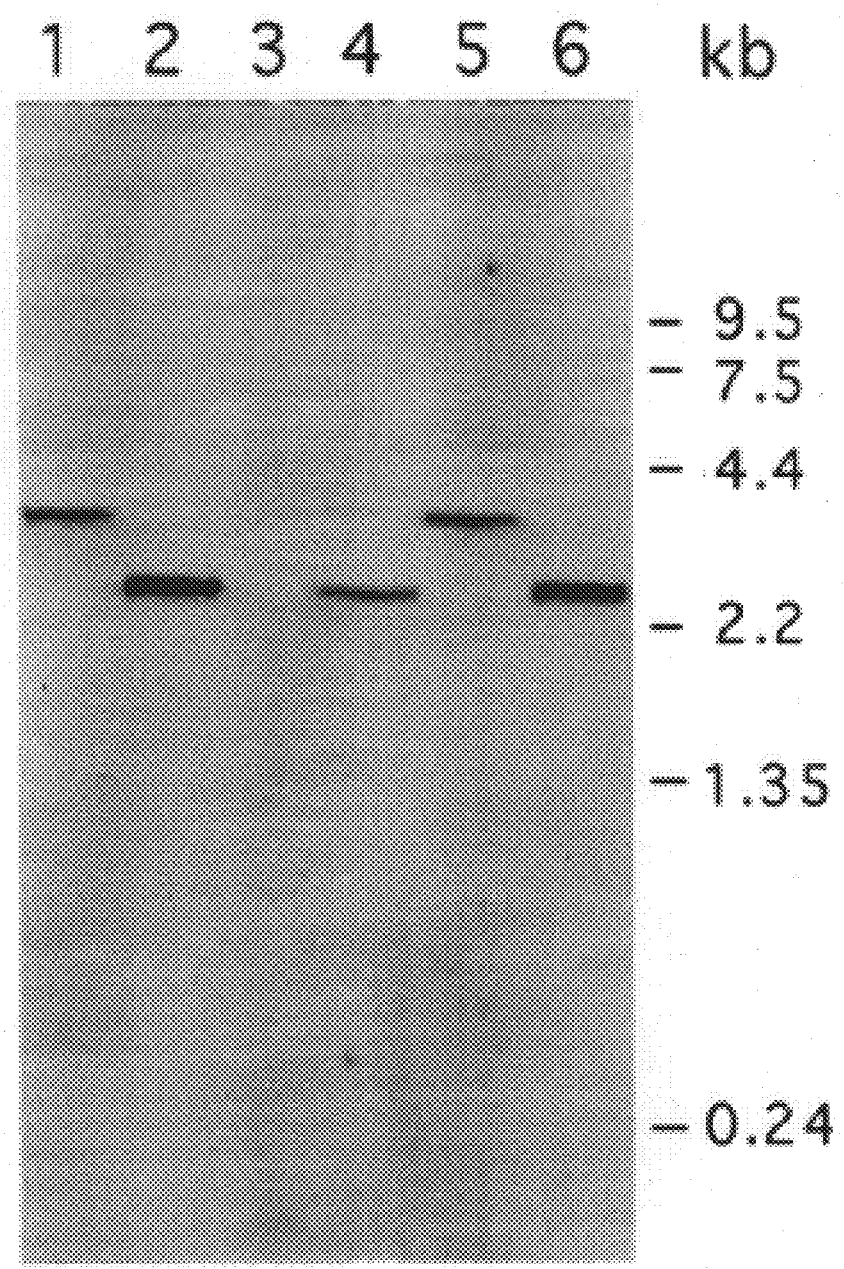
FIG. 10 Levels of ICP4 and ICP0 mRNA in ICP10ΔPK infected cells. mRNA from HSV-2 (lanes 1, 2), ICP10ΔPK (lanes 3, 4) or HSV-2(R) (lanes 5, 6) was hybridized with a [$^{32}$P]-labeled ICP4 (lanes 1,3, 5) or ICP0 (lanes 2, 4, 6) DNA probes. Molecular weight markers are indicated in the margin.

More specifically, because ICP0 protein was observed in ICP10ΔPK infected cells at this time, an ICP0 DNA probe was used as control. Both ICP4 and ICP0 RNA were seen in HSV-2 (FIG. 10, lanes 1,2) and HSV-2(R) (FIG. 10, lanes 5,6) infected cells. ICP4 RNA was not seen in ICP10ΔPK infected cells (FIG. 10, lane 3). The levels of ICP0 RNA in cells infected with ICP10ΔPK for 3 hrs (FIG. 10, lane 4) were only 2-fold lower than in HSV-2 infected cells (FIG. 10, lane 2). We interpret these data to indicate that the failure to observe ICP4 protein in cells infected with ICP10ΔPK is due to the involvement of ICP10 PK in ICP4 transcription.

EXAMPLE 10

ICP10 PK plays a role in inhibition of host cell gene expression and cell lysis

The morphology of the ICP10ΔPK plaques is consistent with incomplete cell lysis. Because ICP27 plays a role in the shut-off of host protein synthesis (Hardwicke et al., J. Virol. 68:4797–4810, 1994) and it is not expressed in cells infected with ICP10ΔPK for 8–12 hrs p.i., we also examined the expression of a host cell gene (actin) in cells infected with HSV-2 or ICP10ΔPK. Vero cells were mock infected or infected with HSV-2 or ICP10ΔPK at moi of 200 and assayed for actin expression by immunoblotting with anti-actin antibody. Actin was not seen in HSV-2 infected cells as early as 3 hrs p.i. (FIG. 8C, lane 2). By contrast, actin levels in cells infected with ICP10ΔPK (FIG. 8C, lane 3) were similar to those in mock infected cells (FIG. 8C, lane 1) as late as 12 hrs p.i. These findings are consistent with the observation that CPE is not seen in ICP10ΔPK infected cells until 15–18 hrs p.i. when the compensatory function(s) come into play.

EXAMPLE 11

Intracellular localization of ICP10 and p95 proteins

Figure 11:
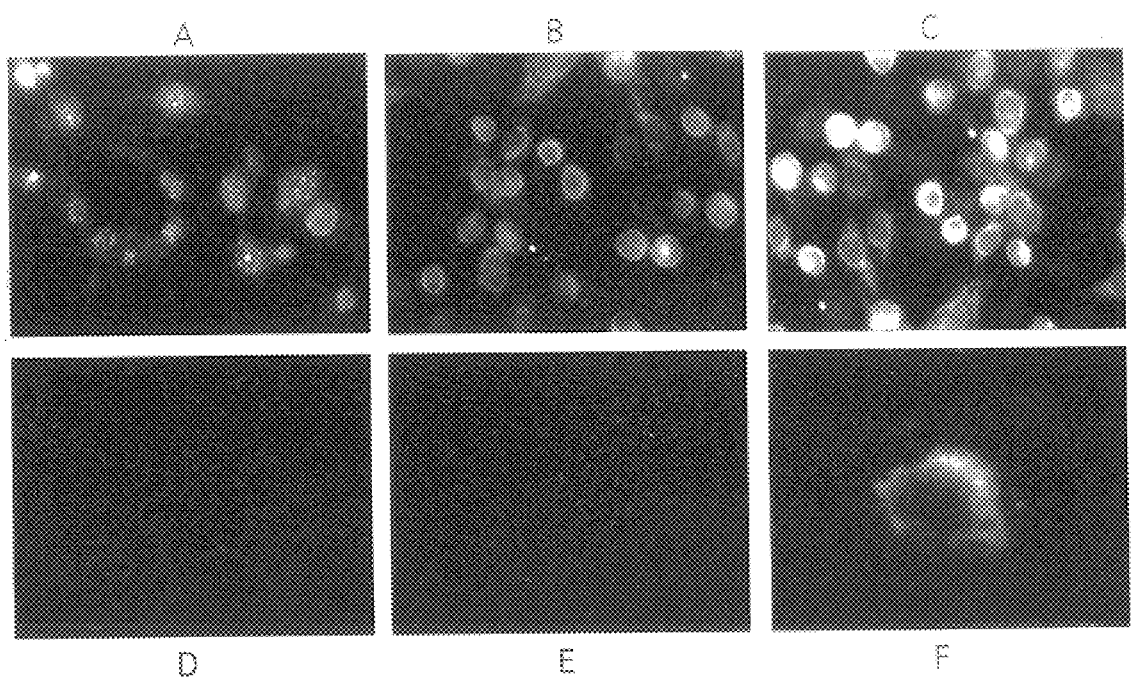
FIG. 11 Indirect immunofluoresecnt staining of Vero cells infected with HSV-2 (Panels A,B,C) or ICP10ΔPK (Panels D,E,F) for 3 hrs (Panels A,D), 6 hrs (Panels B,E) or 9 hrs (Panels C,F) and stained with MAb 30 (Panels A-C) or anti LA-1 antibody (Panels D–F).

Previous studies of cells infected with HSV-2 for 8 and 12 hrs had shown that ICP10 localizes in the cytoplasm and is also associated with the cytoskeleton (Chung et al., J. Virol. 63:3389–3398, 1989). However cells infected for less than 8 hrs were not studied. Because ICP10 PK is required for IE gene expression before 8 hrs, the question arises whether at that time it is also present in the nucleus. Vero cells infected with HSV-2, or HSV-2(R), for 3, 6, or 9 hrs were stained in immunofluorescence with MAb30 (recognizes ICP10 amino acids 106–178). Cells similarly infected with ICP10ΔPK were stained with anti LA-1 antibody (recognizes ICP10 amino acids 13–26). Strong intranuclear staining was seen in cells infected with HSV-2 for 3 hrs (FIG. 11A). It had a punctate appearance consisting of discrete spherical structures (granules) similar to those previously described for viral replication compartments (Rice et al., J. Virol 68:988–1001, 1994; Mullen et al., J. Virol. 68:3250–3266, 1994). At later times p.i., staining took the characteristic perinuclear and diffuse cytoplasmic pattern previously described for ICP10 (FIG. 11B,C). Similar staining patterns were seen for HSV-2(R) (data not shown). By contrast, in ICP10ΔPK infected cells, staining was not seen before 9 hrs p.i. (FIG. 11D,E), at which time it was localized only in the cytoplasm (FIG. 11F). Nuclear staining was also not seen in ICP10ΔPK infected cells at 12 or 15 hrs p.i. (data not shown). These findings suggest that the PK domain of ICP10 is required for nuclear localization early in infection (before 6 hrs).

EXAMPLE 12

ICP10ΔPK virus is attenuated for growth in infected animals

We used the mouse footpad model of HSV-2 infection, in order to examine the role of ICP10ΔPK in virus growth in vivo. Swiss-Webster mice were inoculated s.c. in the footpad with 5×10$^6$ pfu of HSV-2, ICP10ΔPK or a restored virus designated HSV-2(R). Neurological symptoms and severe skin lesions were seen in mice given HSV-2 or HSV-2(R), beginning on day 6 p.i. ICP10ΔPK infected mice had no neurological symptoms nor skin lesions. HSV-2 and HSV-2(R) were isolated from the footpad and ganglionic homogenates for 7–9 days p.i. ICP10ΔPK was only isolated for 4 days p.i. Maximal titers were lower for ICP10ΔPK than HSV-2 (4.3×10$^6$ and 3×10$^7$ pfu for ICP10ΔPK and HSV-2 respectively), and the proportion of latently infected ganglia yielding virus was 90% and 80% for HSV-2 and HSV-2(R) as compared to 0% for ICP10ΔPK (Table 1). These data suggest that ICP10 PK is involved in acute infection and directly, or indirectly, in latency reactivation/establishment.

TABLE 1

Growth and latency reactivation of ICP10ΔPK

| Mean virus titer in footpads (pfu/ml)$^a$ | | | | | |
|---|---|---|---|---|---|
| Day 2 | Day 3 | Day 4 | Day 5 | Day 7 | Latency$^c$ (%) |
| 1 × 10$^3$ | 1.5 × 10$^4$ (+)$^b$ | 2 × 10$^7$ (+) | 3 × 10$^7$ (+) | 1 × 10$^7$ (+) | 9/10 (90) |
| ND | 2 × 10$^4$ (+) | 8.2 × 10$^6$ (+) | ND | 6.1 × 10$^6$ | 8/10 (80) ICP10ΔPK 6.3 × 10$^2$ 2.5 × 10$^3$ (+) 4.3 × 10$^6$ (+)-(−)-(−) 0/10 (0) |

$^a$Mice (groups of 10) were infected with 5 × 10$^6$ pfu of the respective viruses in the footpad. Virus titers were determined by plaque assay on Vero (HSV-2, ICP10ΔPKr) or Vero-ICP10 (ICP10ΔPK) cells. Lesions were first seen on day 7 p.i. in HSV-2 and ICP10ΔPKr infected mice.
$^b$On days 3, 4 and 5 p.i. ganglia were homogenized and assayed for virus presence. (+) means virus was isolated; (−) means virus was not isolated.
$^c$Latency is no of explanted ganglia positive for virus at 30 days p.i/no tested
ND, not done

EXAMPLE 13

ICP10ΔPK virus protects from HSV-2 challenge

Two groups of 10 mice each were respectively mock-infected with phosphate-buffered saline (PBS) or ICP10ΔPK ($5 \times 10^5$ pfu) by one sc injection in the footpad. They did not develop any visible symptoms. On day 16 p.i they were challenged with $3 \times 10^7$ pfu of HSV-2. All mice in the PBS group developed lesions consisting of swelling and redness, first visible on day 5 p.i. and virus (HSV-2) was isolated from the footpads of 10/10 infected mice. On day 15 p.i., 5/10 (50%) of the mice in the PBS group developed paralysis. Mice immunized with ICP10ΔPK virus did not develop visible lesions. Virus was isolated from the footpad in 3/10 (30%) animals. Virus was not isolated from the footpads of 7/10 (70%) of the ICP10ΔPK immunized mice.

TABLE 2

Protection mediated by ICP10ΔPK

| Immuni-zation | Lesions | Challenge | Lesions after immunization | HSV-2 isolation |
|---|---|---|---|---|
| PBS | None | HSV-2 ($1 \times 10^7$ pfu) | 10/10 | 10/10 |
| ICP10ΔPK ($5 \times 10^5$ pfu) | None | HSV-2 ($1 \times 10^7$ pfu) | 0/10 | 3/10 |

Mice (groups of 5) were immunized with low titers of ICP10ΔPK (one s.c. Injection).
Controls were given PBS (not immunized) and challenged with high titers of HSV-2.

These findings indicate that immunization with relatively low doses of ICP10ΔPK protects from challenge with high doses of HSV-2. There is absolute protection in terms of lesion development, in that skin lesions were seen in all unimmunized mice as compared to no lesions in immunized mice. Non-immunized mice were not protected from virus replication, with virus being isolated from all animals on day 5 post challenge. Immunized mice were protected, with virus being isolated from only 3/10 (30%) of the animals.

EXAMPLE 14

ICP10ΔPK virus induces HSV specific immunity

Figure 12:
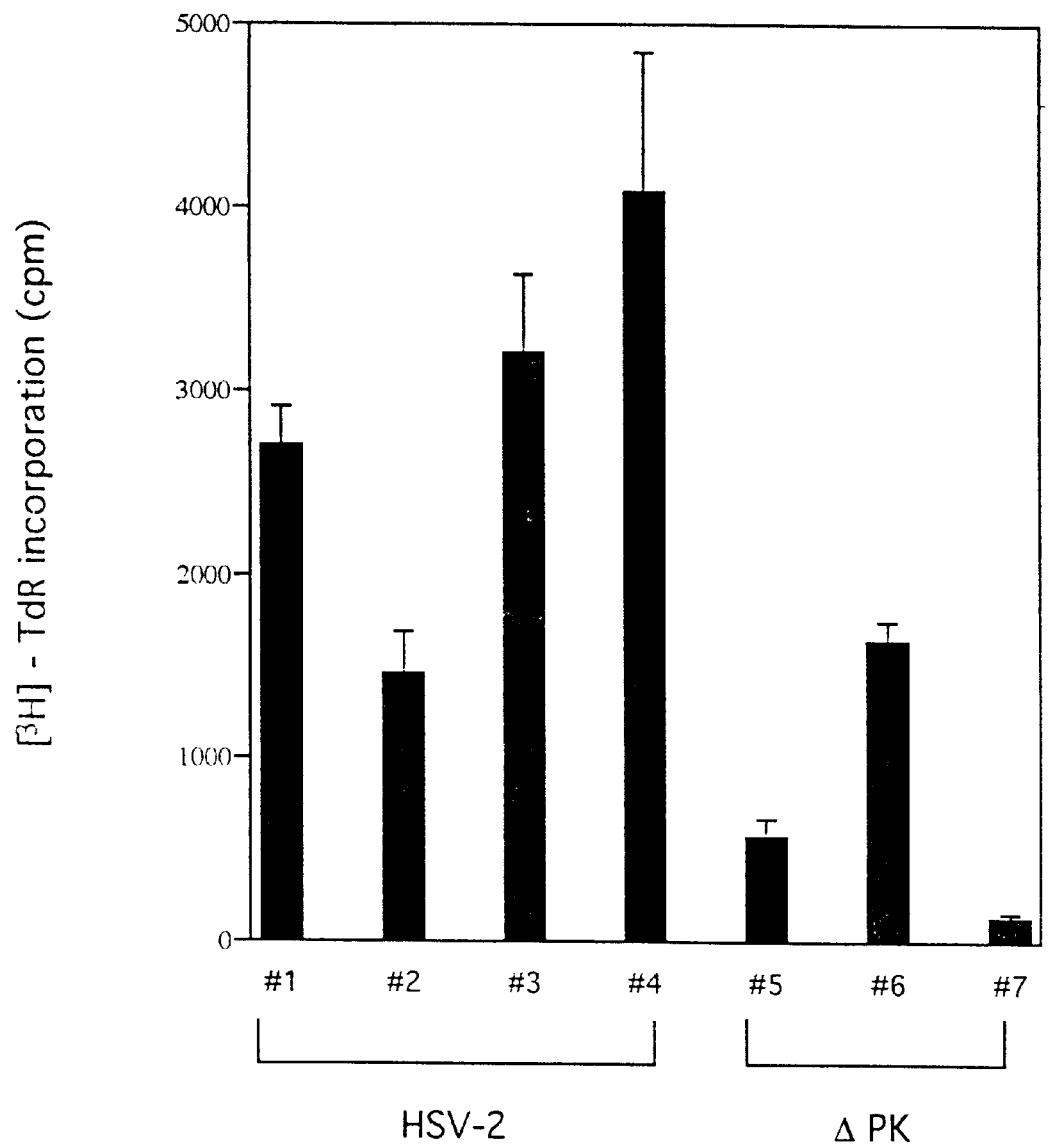
FIG. 12 HSV-2 specific lymphocyte proliferation (Spleen T-cells) in animals immunized with HSV-2 or ICP10ΔPK.

Two groups of 4 mice each were immunized with HSV-2 or ICP10ΔPK ($5 \times 10^5$ pfu) by one sc injection in the footpad. On day 24 p.i, spleens were removed and T cells were used in lymphocyte proliferation assay with HSV-2 antigen as we previously described (Wachsman, et al., Bioscience Reports, 8:323–334, 1988; Wachsman, et al., J. Inf. Dis. 159:625–634, 1989; Wachsman, et al., Vaccine 10:447–454, 1992). This assay measures the development of HSV-specific memory. Uninfected cell extracts prepared in parallel to the virus antigen were used as specificity control. As shown in FIG. 12, HSV-specific immunity was induced by ICP10ΔPK virus, even after only one injection at this low dose. The response was only 2–3-fold lower than that seen for HSV-2 under the same conditions.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

We claim:

1. A vaccine composition comprising a live Herpes Simplex Virus-2 wherein the protein kinase domain of ICP10 (SEQ ID NO:2) has been deleted, and a pharmaceutically acceptable carrier or diluent.

2. A method of immunizing a subject against Herpes Simplex Virus-2 comprising adminstering to said subject the vaccine composition of claim 1.

3. A method of confering immunity against HSV-2 in a subject comprising administering the vaccine composition of claim 1.

4. A method of preventing clinical symptoms in a subject associated with Herpes Simplex Virus-2 comprising administering the vaccine composition of claim 1.

5. The method of claim 2, 3, or 4 wherein said subject is a human.

6. The method of claim 5 wherein the dosage range for said vaccine is 1 to 100 million pfu.

7. The method of claim 5 wherein said vaccine composition is administered via an intranasal, oral, intravaginal, or subcutaneous route.

8. The method of claim 6 wherein the dosage range for said vaccine is 1000 to 75 million pfu.

9. The method claim 6 wherein the dosage range for said vaccine is 10,000 to 50 million pfu.

* * * * *